United States Patent [19]
Anderson et al.

[11] Patent Number: 5,735,844
[45] Date of Patent: Apr. 7, 1998

[54] HAIR REMOVAL USING OPTICAL PULSES

[75] Inventors: R. Rox Anderson, Lexington; Melanie Grossman, Boston; William Farinelli, Danvers, all of Mass.

[73] Assignee: The General Hospital Corporation, Boston, Mass.

[21] Appl. No.: 593,565

[22] Filed: Jan. 30, 1996

Related U.S. Application Data

[63] Continuation-in-part of Ser. No. 382,122, Feb. 1, 1995, Pat. No. 5,595,568.

[51] Int. Cl.$^6$ ........................................ A61N 5/06
[52] U.S. Cl. ................................................ 606/9
[58] Field of Search ........................... 606/8, 9, 10, 11, 606/12, 13, 15, 16, 17, 36, 43, 44

[56] References Cited

U.S. PATENT DOCUMENTS

| | | | |
|---|---|---|---|
| 3,538,919 | 11/1970 | Meyer | 128/398 |
| 3,693,623 | 9/1972 | Harte et al. | |
| 3,834,391 | 9/1974 | Block | |
| 3,900,034 | 8/1975 | Katz et al. | 128/395 |
| 4,388,924 | 6/1983 | Weissman et al. | |
| 4,461,294 | 7/1984 | Baron | |
| 4,608,978 | 9/1986 | Rohr | |
| 4,617,926 | 10/1986 | Sutton | |
| 4,819,669 | 4/1989 | Politzer | 606/9 X |
| 5,000,752 | 3/1991 | Hoskin et al. | 606/9 |
| 5,057,104 | 10/1991 | Chess | 606/9 |
| 5,059,192 | 10/1991 | Zaias | 606/9 |
| 5,182,857 | 2/1993 | Simon | 606/9 X |
| 5,226,907 | 7/1993 | Tankovich | 606/133 |
| 5,282,797 | 2/1994 | Chess | 609/9 |
| 5,344,418 | 9/1994 | Ghaffari | 609/9 |
| 5,425,728 | 6/1995 | Tankovich | 606/9 |

FOREIGN PATENT DOCUMENTS

| | | |
|---|---|---|
| 2 59 902 | 6/1987 | France |
| WO 0 142 671 | 9/1984 | WIPO |
| WO 86/02783 | 9/1986 | WIPO |
| 9515725 | 6/1995 | WIPO ........... A61B 17/41 |

OTHER PUBLICATIONS

Anderson, R. R. and J. A. Parrish, M.D., "Selective Photothermolysis: Precise Microsurgery by Selective Absorption of Pulsed Radiation," *Science*, 220:524–527, 1983.

Anderson, R. R. and J. A. Parrish, M.D., "The Optics of Human Skin." *The Journal of Investigative Dermatology*, 77(1):13–19, 1981.

Dover J. S., et al., "Pigmented Guinea Pig Skin Irradiated With Q–Switched Ruby Laser Pulses." *Arch Dermatol*, 125:43–49, 1989.

Goldman, L., *Biomedical Aspects of the Laser.* New York, Springer–Verlag, 1967, pp. iii–11, 220–232.

Goldman, L., "Dermatologic Manifestation of Laser Radiation." *Fed Am Soc Exp Biology*, Suppl. 14:S–92–S–93, 1965.

Goldman, L., "Effects of New Laser Systems on the Skin." *Arch Dermatol*, 108:385–390, 1973.

(List continued on next page.)

*Primary Examiner*—Jennifer Bahr
*Assistant Examiner*—Sonya Harris-Ogugua
*Attorney, Agent, or Firm*—Wolf, Greenfield & Sacks, P.C.

[57] ABSTRACT

A method and apparatus for simultaneously effecting the removal of multiple hairs from a skin region by using light energy to destroy hair follicles in the region. Light energy is applied to the region through an applicator which converges the light energy to enhance destruction of desired portions of the follicles, is preferably pressed against the skin region to deform the upper layers of the skin reducing the distance from the skin surface to portions of hair follicles which are to be destroyed, including the bulge and papilla of the follicles, and which applicator is preferably cooled to minimize or eliminate thermal damage to the epidermis in the region being irradiated. Parameters for the irradiation, including pulse duration, are selected to effect complete damage of desired portions of the hair follicles in the region with minimal damage to surrounding tissue and to the patient's epidermis.

32 Claims, 8 Drawing Sheets

OTHER PUBLICATIONS

Goldman, L., "Laser Surgery for Skin Cancer." *NY State J Med*, 77:1897–1900, 1977.

Goldman, L., "Surgery by Laser for Malignant Melanoma." *J. Dermatol. Surg. Oncol.*, 5(2):141–144, 1979.

Goldman, L., "The Skin." *Arch Environ Health*, 18:434–326, 1969.

Goldman, L. and D. F. Richfield, "The Effect of Repeated Exposures to Laser Beams." *Acta Derm.–Veneoral*, 44:264–268, 1964.

Goldman, L. and J. Rockwell, "Laser Action at the Cellular Level." *JAMA*, 198:641–644, 1966.

Goldman, L. and R. G. Wilson, "Treatment of Basal Cell Epithelioma by Laser Radiation." *JAMA*, 189:773–775, 1964.

Goldman, L., et al., "Biomedical Aspects of Lasers." *JAMA*, 188:302–306, 1964.

Goldman, L., et al., "Effect of the Laser Beam on the Skin." *The Journal of Investigative Dermatology*, 40:121–122, 1963.

Goldman, L., et al., "Effect of the Laser Beam on the Skin. III. Exposure of Cytological Preparations." *The Journal of Investigative Dermatology*, 42:247–251, 1964.

Goldman, L., et al., "Impact of the Laser on Nevi and Melanomas." *Arch Dermatol*, 90:71–75, 1964.

Goldman, L., et al., "Laser Treatment of Tattoos." *JAMA*, 210:163–166, 1967.

Goldman, L., et al., "Long–Term Laser Exposure of a Senile Freckle." *Arch Environ Health*, 22:401–403, 1971.

Goldman, L., et al., "Pathology of the Effect of the Laser Beam on the Skin." *Nature*, 197:912–914, 1963.

Goldman, L., et al., "Preliminary Investigation of fat Embolization from Pulsed Ruby Laser Impacts of Bone." *Nature*, 221:361–363, 1969.

Goldman, L., et al., "Radiation from a Q–Switched Ruby Laser. Effect of Repeated Impacts of Power Output of 10 Megawatts on a Tattoo of Man." *The Journal of Investigative Dermatology*, 44:69–71, 1965.

Goldman, L., et al., "Replica Microscopy and Scanning Electron Microscopy of Laser Impacts on the Skin." *The Journal of Investigative Dermatology*, 52:18–24, 1969.

Grossman, M. C., et al., "Damage to Hair Follicles by Normal–mode Ruby Laser Pulses." *Journal of the American Academy of Dermatology*, 35(6):889–894, 1996.

Grossman, M. C., et al., "Laser Targeted Hair Follicles." *Lasers Med Surg.*, Suppl. 7:221, 1995.

Margolis, R. J., et al., "Visible Action Spectrum for Melanin–Specific Selective Photothermolysis." *Lasers in Surgery and Medicine*, 9:389–397, 1989.

Parrish, J. A., M.D., et al., "Selective Thermal Effects with Pulsed Irradiation from Lasers: From Organ to Organelle." *The Journal of Investigative Dermatology*, 80:75s–80s, 1983.

Polla, L. L., et al., "Melanosomes Are a Primary Target of Q–Switched Ruby Laser Irradiation in Guinea Pig Skin." *The Journal of Investigative Dermatology*, 89:281–286, 1987.

Riggle, G., et al., "Laser Effects on Normal and Tumor Tissue." *Laser Applications in Medicine and Biology*, 1:35–63, 1971.

Shimbashi, T. and T. Kojima,"Ruby Laser Treatment of Pigmented Skin Lesions." *Aesthetic Plastic Surgery*, 19:225–229, 1995.

Taylor, C. R., et al., "Treatment of Tattoos by Q–Switched Ruby Laser." *Arch Dermatol*, 126:893–899, 1990.

Watanabe, S., et al., "Comparative Studies of Femtosecond to Microsecond Laser Pulses on Selective Pigmented Cell Injury in Skin." *Photochemistry and Photobiology*, 53:757–762, 1991.

Watanabe, S., et al., "The Effect of Pulse Duration non Selective Pigmented Cell Injury by Dye Lasers." *The Journal of Investigative Dermatology*, 88:523, 1987.

Welch, A. J., et al., "Evaluation of Cooling Techniques for the Protection of the Epidermis during ND–YAG Laser Irradiation of the Skin." *Neodymium–YAG Laser in Medicine and Surgery*. New York, Elsevier, 1983, pp. 196–204.

Yules, R. B., et al., "The Effect of Q–Switched Ruby Laser Radiation on Dermal Tattoo Pigment in Man." *Arch Surg*, 95:179–180, 1967.

Zeitler, E. and M. L. Wolbarsht, "Laser Characteristics that Might be Useful in Biology." *Laser Applications in Medicine and Biology*, 1:1–16, 1971.

Bartley et al., "An Experimental Study to Compare Methods of Eyelash Ablation," Ophthalmology 94:1286–1289 1987.

Finkelstein et al., "Epilation of Hair–Bearing Urethral Grafts Using the Neodymium:YAG Surgical Laser" J. Of Urology, 146:840–842, 1991.

Gossman et al., "Prospective Evaluation of the Argon Laser in the Treatment of Trichiasis", Opthalmic Surgery, 23:183–187, 1992.

Gossman et al., Experimental Comparison of Laser and CryoSurgical Cilia Destruction:, Ophthalmic Surgery Surgery, 23:179–182, 1992.

Kuriloff et al., "Pharyngoesophageal Hair Growth: The Role of Laser Epilation", Case Reports, 98:342–345 1988.

(Dry Hair)

(Wet Hair)

(Skin)

HAIR REMOVAL USING OPTICAL PULSES

This is a continuation-in-part of application Ser. No. 08/382,122, filed Feb. 1, 1995 now U.S. Pat. No. 5,595,568.

This invention was made with Government support under Contract N00014-91-C-0084 awarded by the Department of the Navy. The Government has certain rights in the invention.

BACKGROUND

This invention relates to methods and apparatus for hair-removal using optical radiation.

Excess hair (hypertrichosis) and/or unwanted hair are common dermatological and cosmetic problems, and can be caused by heredity, malignancy, or endocrinologic diseases, for example hirsutism (i.e., excess hair due to hormones such as androgens). Hair can be temporarily removed using a number of techniques including wax epilation, depilatory creams, and, of course, shaving. Alternatively, hair can be more permanently removed using electrolysis; this process involves insertion of a current-carrying needle into each hair follicle, and is often painful, inefficient, and time consuming.

Optical-based methods, such as the use of laser light, have also been used for hair removal. U.S. Pat. No. 4,388,924, for example, describes irradiation of individual hair follicles using a laser; in this method, heating of the hair's root section causes coagulation in local blood vessels, resulting in destruction of the follicle and thus in removal of the hair. Related techniques, such as those described in U.S. Pat. No. 5,226,907, involve destruction of the follicle by first applying a light-absorbing substance to the region of interest, the light-absorbing substance migrating at least part-way into the follicle, removing the excess light-absorbing substance, and then irradiating the region to heat the substance and thus the follicle to cause destruction of the follicle.

The above prior art techniques suffer from a number of limitations. First, techniques for irradiating an individual hair follicle are time consuming and therefore are generally not practical for removing hairs other than from a very small region or from a region having few hairs situated therein. The procedure can also be painful, particularly if a needle-like element is inserted into the hair follicle to facilitate light energy reaching the bulge and the root or papilla, parts of the hair follicle which must be destroyed in order to prevent regrowth of the hair. Where the irradiation source is not inserted into the follicle, it is difficult to get sufficient energy to the required portions of the follicle to result in destruction thereof without also causing significant damage to the surrounding tissue and thus causing pain and injury to the patient.

While the technique of the latter patent is advantageous in that it permits a number of hairs in a given region to be simultaneously removed, it is difficult with this technique to get the light-absorbing substance or chromophore deep enough into the follicle to effect destruction of the papilla. Further, this technique results in substantial energy being applied to and absorbed by the epidermis and other skin layers in the region being treated, with significantly reduced energy reaching the root or papilla of the follicle. Total destruction of the follicle, and therefore permanent, or at least long term, hair removal is therefore difficult to achieve, particularly without risking damage to the epidermis and other layers of skin within the region.

A need therefore exists for an improved technique for performing hair removal which facilitates optical energy reaching the bulge and base, or root of hair follicles in a region while minimizing damage to the epidermis in the region, thereby minimizing patient discomfort and potential adverse side effects from the treatment.

SUMMARY OF THE INVENTION

In accordance with the above, this invention provides a method and apparatus for the simultaneous removal of a plurality of hairs from a skin region, each of which hairs is in a follicle extending into the skin from the skin surface. The technique involves placing an applicator in contact with the skin surface in the skin region and applying optical radiation of a selected wavelength and of a selected flux through the applicator to the skin region for a predetermined time interval. The applicator is preferably pressed against the skin surface, thereby reducing the distance from the applicator to the papilla of the hair follicles and facilitating destruction thereof. Further, the invention also involves cooling the skin surface in the skin region to a selected depth during the applying of optical radiation to the skin region and/or prior thereto. This allows the papilla of the hair follicles to be significantly heated without damage to the skin surface in the skin region up to the selected depth.

For preferred embodiments, the applicator is utilized to cool the skin surface in the skin region to the selected depth and the selected depth is preferably at least equal to the depth of the epidermis layer of the skin (i.e. the layer of the skin closest to the skin surface). The cooling by the applicator may for example be accomplished by cooling at least the surface of the applicator in contact with the skin surface, such cooling preferably being accomplished both before and during the irradiation of the skin. For preferred embodiments, the cooling of the applicator is accomplished by passing a cooling fluid through the applicator. Further, it is also preferred that irradiation of the skin surface not be performed until the skin region has been cooled to substantially the selected depth. For the most preferred embodiment, cooling is performed both before and during irradiation, and the selected flux and predetermined exposure time (i.e., time interval for irradiation) are selected such that there is at most minimal heating of skin in the skin region to the selected depth, while there is sufficient heating of hairs and follicles below the selected depth to at least damage the hairs and follicles without causing significant damage to tissue surrounding the follicles. A preferred time interval for irradiation is 2 to 100 ms. The applicator is also preferably designed to converge optical radiation applied to the skin region, thereby further facilitating irradiation of the follicle papillas. For preferred embodiments, the applicator also has a convex surface in contact with the skin surface, applying substantially uniform pressure thereto to deform the underlying skin surface. For alternative embodiments, the applicator is designed to form a fold of the skin in the skin region and to apply optical radiation to two substantially opposite sides of the fold. For example, the applicator may have a slot formed in the surface thereof in contact with the skin surface, with at least a portion of the skin region being drawn up into the slot and optical radiation being applied to the skin region from at least two opposite sides of the slot.

It is also desirable that a substantial refractive index match be maintained between the applicator and the skin surface in said skin region. Such refractive index match may be provided by a layer of refractive index matching substance between the applicator and the skin surface in a skin region and/or by forming the applicator of a material which at least for the surface in contact with the skin region has a refractive index which substantially matches that of the skin surface.

To facilitate hair removal, hairs in the skin region may be shaved prior to irradiation. However, it may be preferable to epilate the hairs in the skin region before irradiation. When hairs are epilated, destruction of the follicles can be facilitated by filling the follicles from which the hairs have been epilated with a substance which preferentially absorbs optical radiation at the selected wavelength being used for irradiation (i.e. a chromophore). Further, where only temporary hair removal is desired, this may be accomplished for a period of up to several weeks, relatively painlessly, by applying the chromophore to the area, which has been preferably pre-shaved, which chromophore migrates into the hair follicles to a depth of a few millimeters, roughly to the depth of the sebaceous gland. Low level irradiation applied through the applicator to the skin region will then result in the destruction of the hair without destroying the follicle.

An applicator suitable for use in practicing hair removal in accordance with the above may include an inlet through which optical radiation is applied to the applicator, a surface shaped to contact the skin surface in the skin region, an optical path from the inlet to the surface, which path is substantially transparent to optical radiation at the selected wavelength, an element in the optical path for converging the optical radiation as it leaves the applicator through the surface and some means for cooling the surface to a temperature below that of the skin region. As indicated previously, the surface is preferably formed of a material having a refractive index which substantially matches, but which is not less than, the refractive index of the skin surface in the skin region. For preferred embodiments, the element for converging the optical radiation is a lens and the means for cooling is a channel near the surface through which cooling water is passed. For one embodiment, the surface of the applicator in contact with the skin has a convex shape while for an alternative embodiment the surface has a slot formed therein, with the optical path leading to at least two opposite sides of the slot, and the applicator includes a means for drawing at least a portion of the skin region into the slot, this means for drawing preferably includes a vacuum applying element.

The foregoing and other objects, features and advantages of the invention will be apparent from the following more particular description of preferred embodiments of the invention as illustrated in the accompanying drawings.

DETAILED DESCRIPTION

Figure 1:
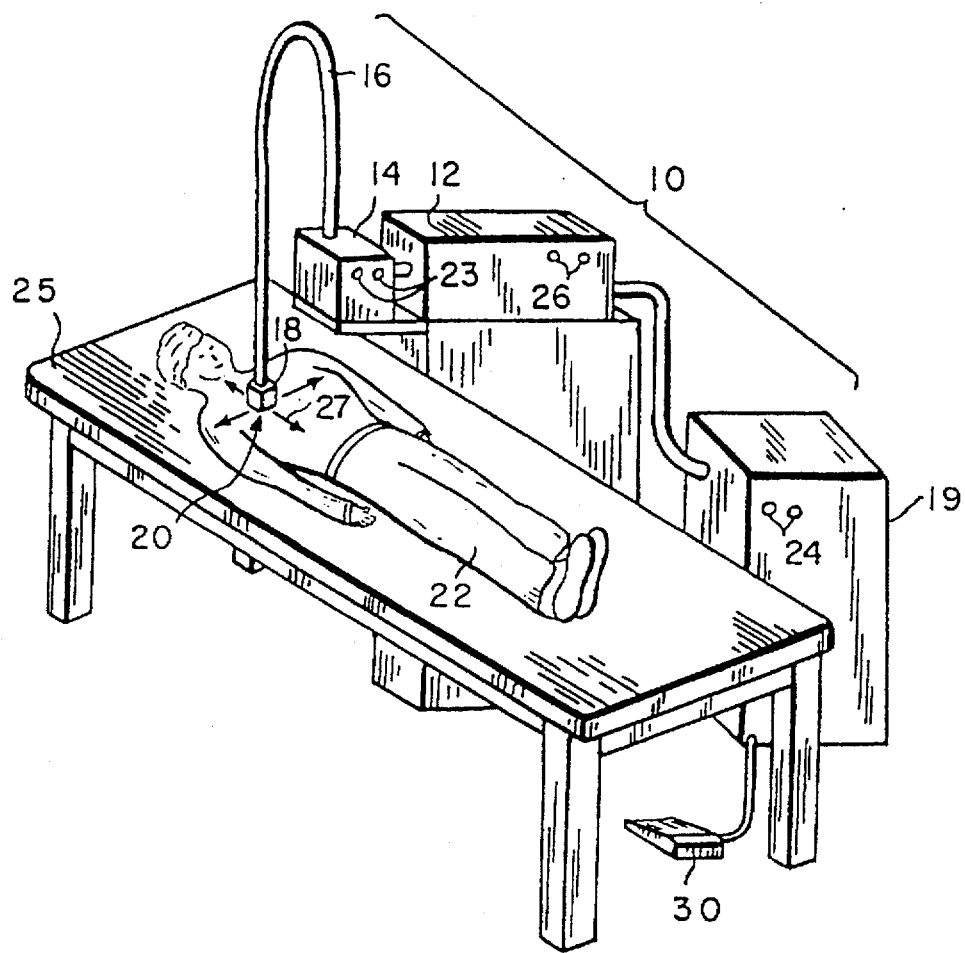
FIG. 1 is a perspective view of a laser-based hair-removal device according to the invention.

Referring to FIG. 1, an exemplary laser-based hair-removal system 10 includes a light source 12, which may, for example, include one or more lasers for generating the irradiating field. The light source 12 may be optically coupled to a series of beam-manipulating optics 14 which, in turn, may be coupled via a fiber optic cable 16 (or other fiber optic device) to the irradiating unit or applicator 18. During the hair-removal therapy, the light source is powered by a voltage and current supply 19, and delivers a beam of light through the optics 14 and fiber optics 16 to the irradiating unit or applicator 18. The field is then delivered to a region 20 of a patient 22 (positioned, for example, on a table 25, a chair, or other suitable positioning element depending on the location of the region 20 on the patient's body) resulting in hair removal from the region 20. Once the desired region is treated, the irradiating unit can be easily moved along the patient 22, as indicated by arrows 27, and used to treat subsequent regions.

The spatial and temporal properties of the optical field determine the efficacy of the hair-removal process, and some of these properties may, if desired, be adjusted using a series of controls 24, 26, 28 located on various components of the hair-removal system 10. For example, using controls 24 located on the power supply, the optical intensity and pulse repetition rate of the irradiating field can be controlled by adjusting parameters such as the voltage, current, and switching rate for the laser's power supply. Other properties of the field, such as the wavelength and pulse duration, may be varied by controls 26 which adjust components (e.g., gratings, mirror or filter positions, shutters, or pulse-forming means) of the light source 12; however, for preferred embodiments wavelength would not be adjusted. Similarly, controls 28 can be used to adjust the modulating optics 14, resulting in control of properties such as mode quality, beam diameter, and coupling of the irradiating field into the fiber optics 16. All controls may be adjusted by hand; and the system may also be operated (i.e. the laser turned on) by hand or, alternatively, by using a foot pedal 30 connected to the system 10.

In alternate embodiments, the light source, coupling optics, and irradiation unit may be encompassed in a single, hand-held device. In this case, the light source is preferably an array of diode lasers coupled directly to the irradiating unit, and is powered by a small external power supply. The compact nature of this type of optical system allows for a more controllable, maneuverable device, and additionally obviates the need for fiber optic delivery systems.

In order to effectively destroy the irradiated hair follicles without causing damage to the surrounding skin, the light field supplied by the system 10 and the irradiating unit 18 is designed to maximize the amount of light-induced heat deposited in the hair follicles, while reducing the degree of injury to the surrounding skin. It is preferred, for example, to deliver sufficient optical energy to several "target" regions on the hair follicle; radiation delivered to these regions results in complete and localized destruction of the follicles.

Prior to treatment, the region to be treated may be shaved in order to facilitate irradiation of the follicles. Alternatively, as will be discussed later, hairs in the region may be epilated and a chromophore may be applied to region 20, which chromophore migrates into the empty follicles. Excess chromophore may then be removed from the skin surface prior to irradiation. Prior to treatment, an anesthetic may also be injected locally or applied to the skin surface and following treatment, patients may be treated with topical antibiotic ointments.

MECHANICAL STRUCTURE

Figure 2A:
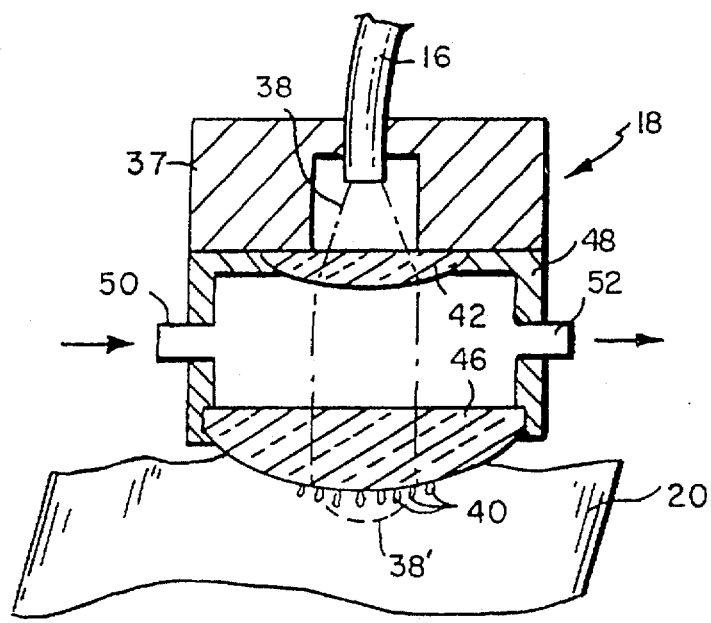
FIGS. 2A and 2B are cross-sectional views of an irradiating unit or applicator suitable for use with a hair-removal device of this invention, the applicator receiving, respectively, light from a fiber optic or fiber optic bundle, and from a mirror assembly.
Figure 2B:
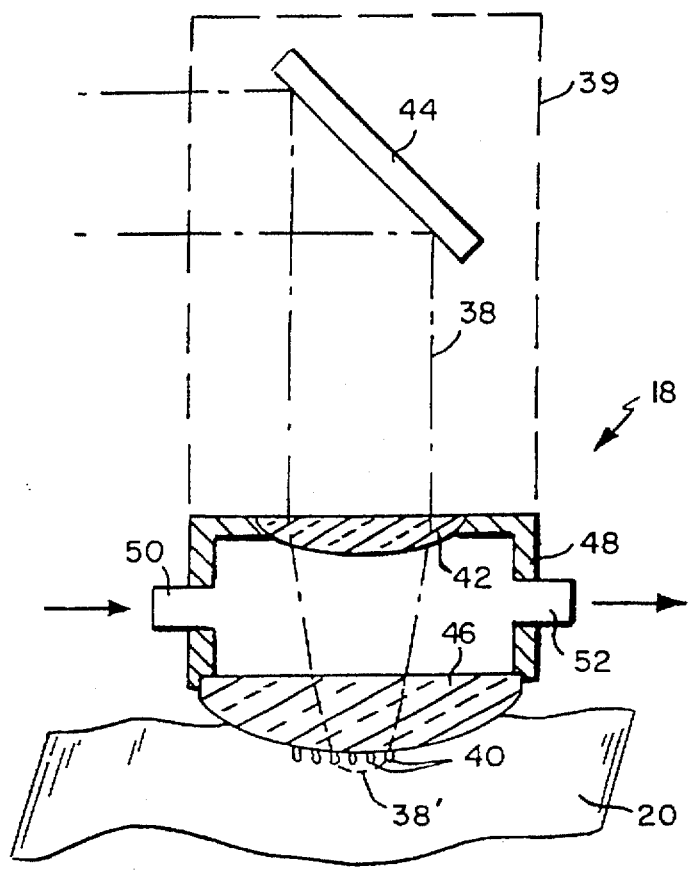

With reference now to FIGS. 2A and 2B, the applicator or irradiating unit 18 of the hair-removal system allows delivery of the irradiating field 38 to hair follicles 40 located in the region 20. As shown in FIG. 2A, the field 38 may be delivered to the irradiating unit 18 using a fiber optic cable 16 (or other fiber optic device) containing one or more fibers or fiber optic bundles. In this case, after exiting the waveguide, the field 38 is typically spatially dispersed, and is preferably collected and roughly collimated using a piano-convex lens 42. Alternatively, as shown in FIG. 2B, the field may be delivered to the irradiating unit using, for example, one or more reflecting mirrors 44. This allows the field 38 to be roughly collimated prior to impinging on the lens 42. Depending on the focal length of the lens 42 and the mode quality of the irradiating field, the field is preferably condensed using, e.g., a plano-convex lens as shown in the figure. After passing through this optic, the beam then impinges on a lens or contact device 46 which is placed in contact with the skin region 20. The optical and mechanical properties of the contact device 46 are chosen to allow efficient coupling of the optical radiation into the skin region (resulting in a delivered field 38) and the thermal properties of the contact device are chosen to allow efficient coupling of heat from the skin region. Once delivered, the field is used to irradiate, heat, and then destroy the hair follicles 40. The contact device 46, in addition, is used to couple light and heat out of the superficial skin layer (i.e., epidermis) of the irradiated region. This allows the light-absorbing pigment (i.e., melanin) contained within the deep part of the hair follicles to be irradiated and selectively heated, permitting permanent destruction of the follicle, while potentially deleterious optical and thermal energy are simultaneously conducted out of the overlying skin layers. Thus, multiple hair follicles can be destroyed, permanently removing hair from the skin region without causing substantial pain or injury to the patient. The destroyed follicles are ultimately removed by the body.

Both the lens 42 and contact device 46 are preferably disposed in a housing 48 containing both entrance 50 and exit 52 ports for fluids such as cooling water and pure gas (i.e., nitrogen to prevent condensation on the lens) to flow into and out of; fluids may be used, for example, to cool the contact device 46, which, in ram, cools the skin surface. Alternatively, the housing 48 may include an electrically controlled cooler in order to provide accurate control over the temperature of the contact device 46. Preferably, when cooling means are used, the temperature of the surface layer or epidermis of the skin is reduced to between 4°–15° C. In addition, in this case, it is preferred that a short time period (e.g., about 1 second) be allowed to elapse before irradiation in order to ensure that the epidermis is adequately cooled. An external casing 39, as indicated in FIG. 2B by the dashed line, or a fiber-coupling housing 37, as shown in FIG. 2A, may be used to connect the light-delivering means to the housing 48.

Figure 3A:
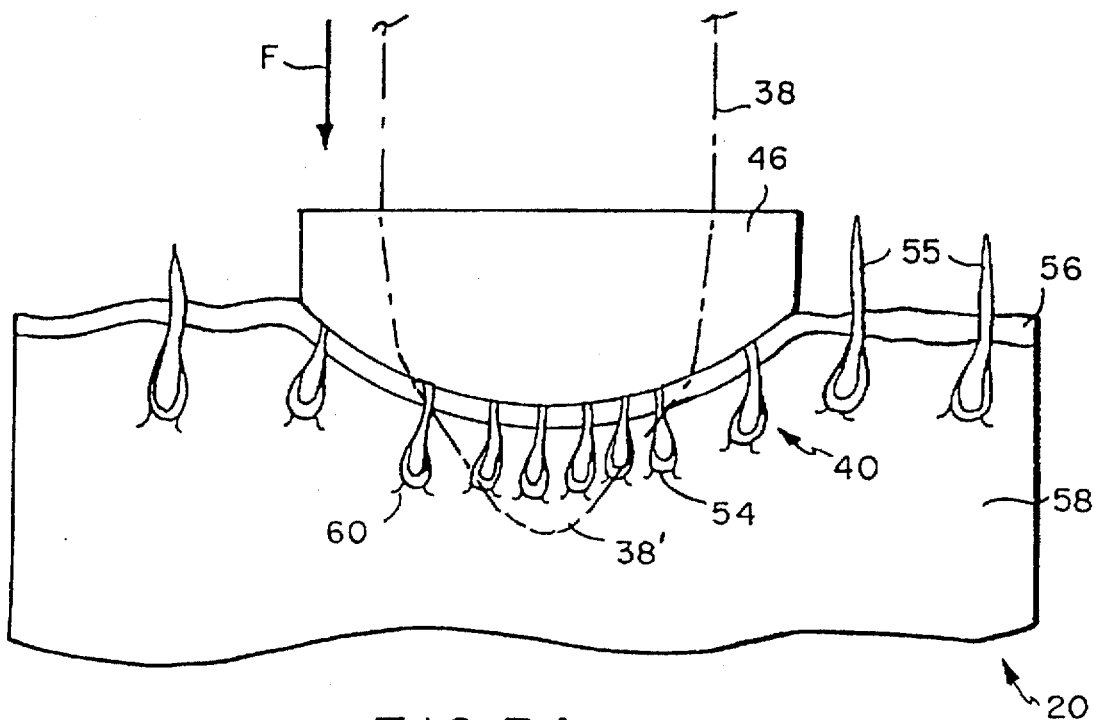
FIGS. 3A, 3B, and 3C are, respectively, an expanded, cross-sectional view of the contact device of the irradiating unit in direct contact with a hair-containing skin region, a cross-sectional, cut-out view showing the back-scattered optical fields at the contact device/epidermis interfacial region, and a cross-sectional cut-out view showing thermal transport at the interfacial region.

With reference now to FIG. 3A, the contact device 46 is preferably formed into a lens shaped in order to converge the irradiating field, preferably near the base of the hair follicles 40. In order to converge light, the contact device must be optically transparent at the irradiating wavelength, and preferably has a biconvex or plano-convex lens shape, preferably with an f number less than or equal to f/1.0, and a focal length of between about 0.5 and 2 cm. Control over the surface shape of the contact device allows the converged light field 38' to simultaneously irradiate various target portions of the hair follicle, resulting in efficient destruction. Typically, each irradiated hair shaft has a diameter of about 75 microns, with the entire follicle having a diameter of about 200 microns. After passing through the contact device 46, the light field 38' is preferably converged through the epidermis 56 of the skin layer (having a thickness, e.g., of about 0.1 mm) and is condensed in the dermis 58 near the papillae 54 of the follicles 40. Because dermal thickness varies greatly over the body, the papillae may be superficial (as in, e.g., the eyelids and scrotum), but for most areas of interest (e.g., the face, axillae, and legs) the papillae are located at depths of approximately 4 to 7 mm beneath the epidermal surface. Located a few tenths of a millimeter below the papillae are neurovascular bundles 60 which serve the metabolic and other needs of a hair matrix, the region of rapidly growing keratinizing cells, located in the papilla, which produce the hair shaft 55. The matrix, papilla, and the corresponding vascular bundle, as well as the bulge near the center of the follicle, represent the follicular targets to be irradiated/destroyed. Preferably, during irradiation of these regions, the field is pulsed, the pulse duration of the irradiation being kept short enough so that damage is localized to a small region of dermis (typically within about 0.2 mm) surrounding each follicle in accordance with the principles of selective photothermolysis. The extent of damage is preferably much less than half the distance between neighboring follicles (typically between 1 and 4 mm); if it is significantly greater than this, the light-induced injury may result in a third-degree burn.

In addition to providing a light converging function, a contact device 46 having a convex-shaped surface 62 allows efficient compression of the skin during contact. Compression of the dermis 58 located near the surface 62 of the contact device decreases the distance between this region and the papillae; depending on the force applied, the distance may be decreased by up to several millimeters. Because the radiation field 38' is scattered and correspondingly attenuated during propagation through the dermis, compression of the skin results in bringing more light to the deep portions of the hair follicles for more efficient light-induced heating of the papilla. In addition, compression of the dermis by the contact device using a pressure greater than the patient's blood pressure forces light-absorbing blood out of the irradiated region (indicated during treatment by a whitening of the skin in the pressurized region). This reduces absorption of the optical field, resulting in more efficient delivery of light to the follicular target regions. Pressure applied using a contact device having a convex surface results in a relatively uniform displacement of blood from the skin region. A contact device having this shape is therefore preferred to a flat device, which tends to produce regions having center portions which are not entirely blood-free.

In alternate embodiments, the contact device may be mounted in the housing in a spring-loaded fashion so that it may be forced against the skin surface with an adjustable pressure. In addition, in this embodiment, the spring mechanism may be attached to a sensor and readout device so that the exact pressure applied to the skin surface can be accurately monitored and/or controlled.

Figure 3B:
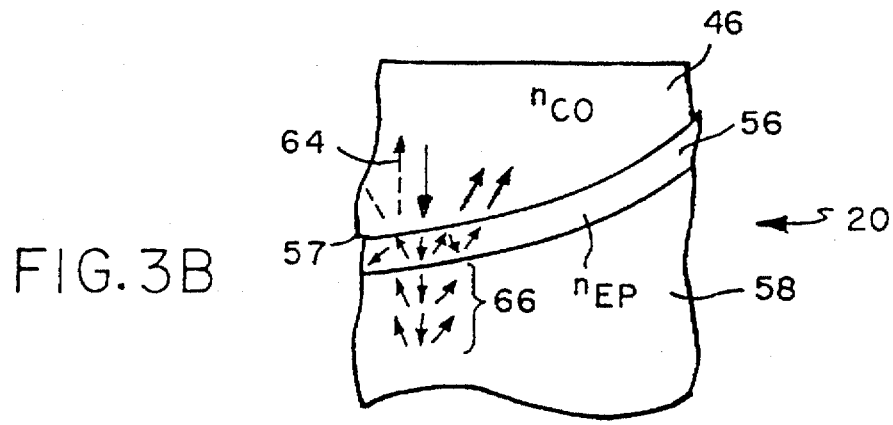

When forced against the skin, the contact device 46 allows optical radiation to be coupled into and out of the epidermis. With reference now to FIG. 3B, the refractive index ($n_{CD}$) of the contact device 46 should be approximately matched to that ($n_{EP}$) of the epidermis 56, which is approximately 1.55. Because light travelling from one refracting media (i.e., the contact device) to another (the epidermis) is reflected at the interface 57 separating the two regions by an amount related to the square of the refractive index difference, nearly index-matching allows efficient coupling of the irradiating field into the skin. Thus, a contact device composed of a material having a refractive index near 1.5 or somewhat greater allows the incident irradiating field to undergo minimal reflections (indicated in the figure by the arrow 64) at the epidermis/contact device interface 57. Similarly, as indicated in the figure by the arrows 66, optical fields within the dermis are back-scattered towards the epidermis due to diffuse reflectance. These back-scattered fields contribute to unwanted epidermal heating, and are easily coupled out of the skin using the index-matched contact device 46. This allows minimization of the light-induced damage to the epidermis 56, while allowing effective irradiation of the follicle target silos within the dermis. In preferred embodiments, in order to be substantially index-matched, the contact device is preferably formed of a high-density material such as sapphire ($n_{CD}=1.7$), fused silica ($n_{CD}=1.5$), or similar optically transparent glasses or plastics. In order to provide a convergent field entering the skin and to have the convex shape of the contact device as shown, it is advantageous to use sapphire, the slightly higher index of which facilitates the desired field convergence.

Figure 3C:
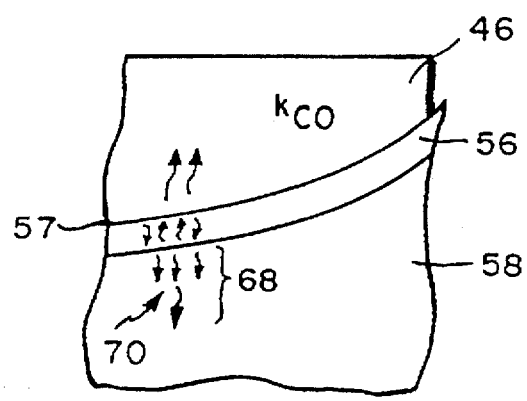

With reference now to FIG. 3C, in order to conduct heat away from the epidermis, it is additionally preferred that the contact device 46 be composed of a material having a high thermal conductivity ($k_{CD}$) which is similar to that of the skin. This allows efficient transfer of heat (indicated in the figure by the arrows 68) from the epidermis 56, across the contact device/epidermis interface 57, and into the contact device 46. A high thermal conductivity, in addition, is necessary to minimize local heating effects that may occur at the interface 57, thereby reducing the chance of thermally induced damage or injury to the irradiated epidermis. As will be discussed later, this is particularly important when the contact device is cooled. Ideally, the thermal properties of the contact device and the time the contact device is applied to the skin before irradiation begins allow minimization of heating near the epidermis, but have little effect on heat deposited near the papillae of the hair follicle (shown in the figure as region 70). Materials having high thermal conductivities include sapphire ($K_{CD}=0.083$ cal sec$^{-1}$ cm$^{-2}$°C. cm$^{-1}$ along the C axis at 30° C.), fused silica ($K_{CD}=0.026$ cal sec$^{-1}$ cm$^{-2}$ °C. cm$^{-1}$ along the C axis at 30° C.), as well as other high-density glasses and plastics.

In addition, in order to improve both optical (i.e., transmission of back-scattered light) and thermal (i.e., heat conduction) properties at the contact device/epidermis interface 57, it is desirable to apply to the skin a topical liquid or emollient, such as a lotion, water, alcohol, or oil, having a refractive index which is similar to that of the contact device 46 and epidermis. For example, application of an oil having a refractive index between that of the epidermis (n=1.55) and sapphire (n=1.7) minimizes optical reflection effects at the interface, thereby allowing more efficient transfer of light into the skin region from the contact device and of back-scattered radiation from the skin region. Also, a liquid allows for more efficient transfer of heat by conduction from the skin into the sapphire, thereby reducing the degree of damage or injury to the epidermis.

OPTICAL PROPERTIES

The temporal and spatial distribution of intensity for the irradiating optical field inside the skin ultimately determine the amount of heat deposited into the target regions of the hair follicle; these properties therefore can be selected and/or adjusted to optimize the hair-removal process. In particular, properties which affect the hair-removal process include the pulse energy, pulse duration, repetition rate (i.e., the time duration between subsequent pulses), wavelength, energy, exposure spot size, beam convergence as it enters the skin, and mode geometry (i.e., spatial extent and uniformity) of the optical pulse. These characteristics may be selected according to the pigment present in the hair and skin to be irradiated; preferably, each parameter is adjusted so that the temperature at each target site, immediately following irradiation, is elevated to between about 80° and 120° C. Heating the follicle to this temperature leads to permanent damage and subsequent removal.

Figure 4:
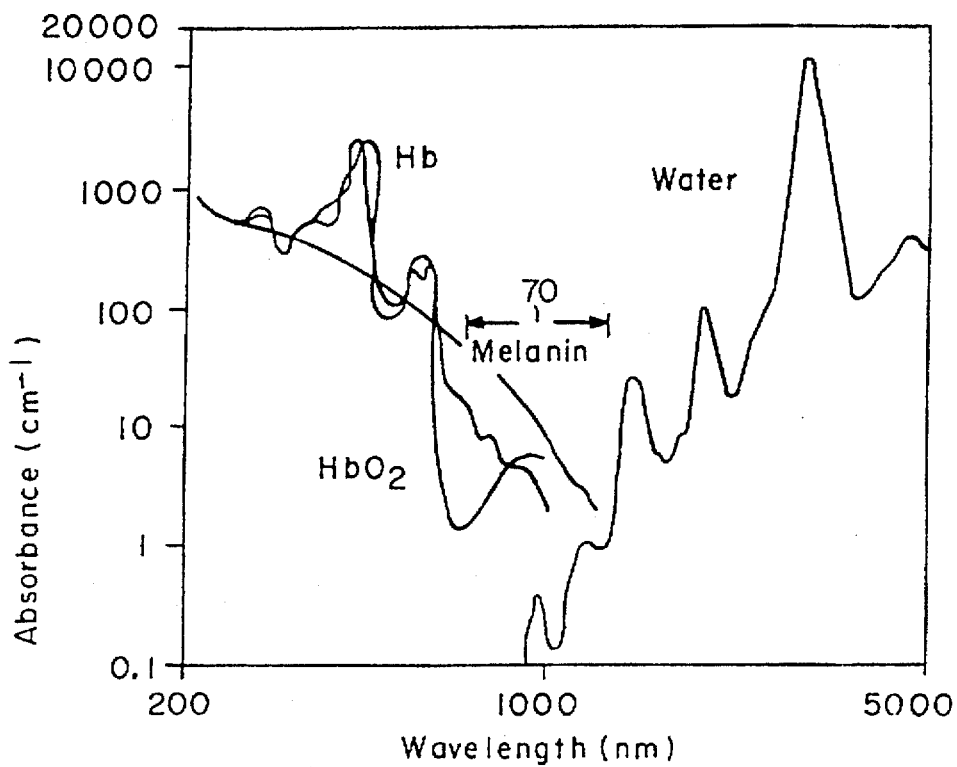
FIG. 4 is a plot showing the optical absorption spectra of melanin, hemoglobin, oxygenated hemoglobin, and water.

Referring now to FIG. 4, the wavelength of the irradiating field is chosen to be resonant with the natural pigment (i.e., melanin) present in the target sites (i.e., the hair shaft, bulge, matrix, and papilla). The absorption spectra of melanin, water, hemoglobin, and oxyhemoglobin shown in the figure indicate the ability of these compounds to absorb optical radiation at different wavelengths; low absorption indicates that light at the particular wavelength will penetrate deeper in the absorbing media. In general, in order to selectively heat the target regions, the wavelength of the irradiating field is chosen to match the absorption spectrum of melanin, which basically absorbs light from about 200 to 1200 nm; conversely, the wavelength is mismatched to the absorption spectra of compounds contained in the skin, such as water and hemoglobin. Light having wavelengths between 680 and 1200 nm, a range indicated by the arrow 70 in the figure, is effectively absorbed by melanin while being relatively transmitted by both hemoglobin and water, and therefore can be used for selective heating of pigmented hair surrounded by white or lightly tanned skin. In particular, light in the range of 680 to 900 nm or 1000 to 1200 nm is preferred, as this radiation is strongly absorbed by melanin, and will not be absorbed by the bands present in water and in oxyhemoglobin near 950 nm. For patients with less melanin present in the hair follicles (e.g. with auburn or light brown hair), the shorter wavelengths in this region are preferable because of the higher absorption coefficient of melanin. In addition, other light-attenuating effects besides absorption, e.g., scattering of radiation, are also wavelength-dependent, and should be considered during selection of the optical field's wavelength. For example, in human skin, the penetration of light is partially determined by the transport scattering coefficient ($\mu_s$), which decreases at longer wavelengths due to scattering in the dermis. For radiation at 1000 nm, $\mu_s$ is about 10 cm$^{-1}$; light propagating into the skin from a generally index-matched medium at this wavelength will therefore reach a maximum intensity at about 1 mm below the skin surface.

Sources generating visible or near-infrared light in the preferred range of 680–1200 nm include diode ($\lambda \approx 800-1000$ nm), Nd:YAG and Nd:YLF ($\lambda=1064$ and 1053 nm), Ti:Sapphire and infra-red dye ($\lambda \approx 700-1000$ nm), ruby ($\lambda=694$ nm) and alexandrite ($\lambda=700-850$ nm) lasers. Ruby, Nd:YAG and diode lasers (particular arrays of diode lasers) are preferred as these sources are commercially available, well-categorized, and can be manufactured on a small scale. Light sources of this type can be incorporated into compact hair-removal devices which, in turn, can be easily manipulated by the operator during hair-removal procedures.

Figure 5A:
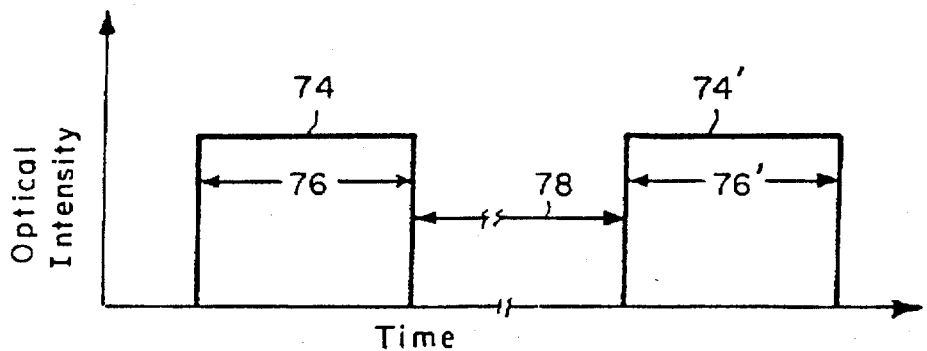
FIGS. 5A and 5B show, respectively, the time and spatial profiles and the preferred optical field used during the hair-removal process.

The duration of the optical pulse can also be controlled in order to vary the heating of the hair follicle. Referring now to FIG. 5A, the optical pulses, indicated by the waveforms 74,74', preferably have durations 76,76' which allow the follicle to be heated for short periods of time. The pulse width is controlled to vary the heat conduction during the optical pulse, and thus the damage of the follicle and its immediate surrounding dermis; too little damage results in hair re-occurrence, while extensive damage may produce scarring in the irradiated region. Preferably, the pulse duration 76, 76' is between about 2 ms and 100 ms.

The exact pulse duration is dictated by the diffusion of heat in the skin, a process which roughly follows the heat diffusion equation relating the diffusion time t, diffusion distance d, and thermal diffusivity k, as discussed by in Welch, A. J. "The thermal response of laser-irradiated tissue", IEEE J. Quant. Electron. QE–21 (12), 1471–1481 (1984):$t=d^2/4k$ (k for the human dermis is roughly $1.3 \times 10^{-3}$ cm$^2$/sec). The time needed for extraction of heat from the epidermis during a laser pulse is approximately 2 ms, and the thermal relaxation time for a typical 200 micrometer hair follicle is approximately 40 ms. For light exposures longer than a few hundred milliseconds, too much thermal diffusion may occur during the exposure period, resulting in either inefficient destruction of the target regions of the hair follicle, excessive dermal damage, or both. Further, since most of the melanin (roughly two thirds) in the epidermis is in the lower portion of the epidermis, heating of the epidermis occurs primarily in the deeper portions thereof, and some time is required for this heat to reach the surface in order to be removed by the contact device 46. Therefore, since this time is at least 2 ms, this is the minimum suggested pulse duration, with a longer time, preferably at least 5 ms, being suggested to minimize epidermal damage. Further, depending on the laser utilized, each pulse could be in the form of a single continuous pulse as shown in FIG. 5A or in the form of a train of closely spaced pulses of shorter duration, the space between such closely-spaced pulses being much shorter than 5 ms.

For a given fluence, the intensity of the optical field is inversely related to the pulse duration; thus, when the pulse duration is below about 10 μs, large optical intensities may result in undesirable modes of damage to surrounding skin regions. In addition, short pulses may result in localized heat-induced "explosions" in the follicle which cause mechanical damage to the skin. In particularly preferred embodiments, the pulse has a duration or pulse-width of about 2–100 ms. During this time period, thermal diffusion takes place over a distance of about 0.05 to 0.3 mm; damage confined to about this distance results primarily in destruction of the irradiated hair follicles, with little or no damage to the surrounding skin.

Optical pulses having well-defined and adjustable durations may be generated using known techniques. For instance, intra-cavity modulation of the light field using electro or acousto-optic Q-switching devices allows generation of pulses having temporal profiles which are typically Gaussian in shape. Pulses made using these methods are typically too short, however, having durations in the sub-microsecond range. Normal-mode pulses produced by flashlamp excitation of ruby, alexandrite, Ti:sapphire, or Nd:YAG lasers are preferred because these typically are high-energy pulses in the 0.1–10 ms pulse duration region. Alternatively, a continuous (i.e., time-independent) optical field emitted by a laser can be externally modulated using, for example, a mechanical shutter or electro-optic gate. Modulation using external methods allows the pulse width to be easily varied from a few hundred microseconds to several hundred milliseconds. Pulses generated using external modulation may also have "square wave" temporal profiles (as shown in FIG. 5A) which allow a more uniform optical field to be applied to the region of interest. However, external modulation is not used for currently preferred embodiments.

When a contact device is used to deliver the optical pulse, a time delay preferably exists between the time at which the contact device contacts the skin surface and the arrival of the pulse. This allows the entire epidermal layer 56 to be cooled significantly prior to irradiation, thereby increasing its damage threshold. Pain and damage to the epidermis are thus reduced and are further minimized by continuing to cool contact device 46 during irradiation so that heat continues to be removed from the epidermis. However, heating at lower levels where destruction of the follicles, and in particular the bulge and papillae thereof, is desired is not affected by the cooling performed either before and/or during irradiation.

In addition, the time duration between optical pulses (indicated in FIG. 5A by the arrow 78) may be adjusted in order to control the total amount and rate on average of heat deposited into the irradiated region. If repetitive illumination is required for destruction of the follicle, this time period is preferably constant and lies between several seconds and a few hundred milliseconds. Alternatively, for "single shot" illumination, this time period is selectively controlled by the operator. In this case, a single laser shot is delivered to the region of interest, and then the region is inspected by the operator for damage. If more radiation is required, additional laser shots can then be delivered to the region. Otherwise, the irradiation unit is translated and used to treat a separate region.

Figure 5B:
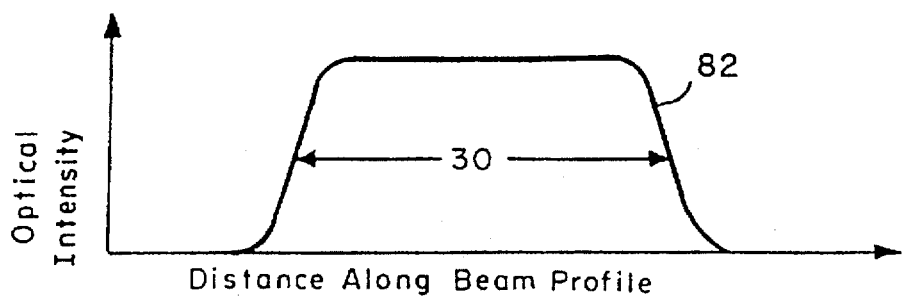

The spatial extent of the optical field is chosen to allow multiple hair follicles to be irradiated with a single laser shot. In addition, larger spot sizes are preferred because attenuation along the beam axis within skin due to scattering decreases as the beam radius, R, increases. Thus, wide-area beams allow more efficient delivery of optical radiation to the deep target sites. Referring now to FIG. 5B, the width 80 of the spatial profile 82 of the irradiating beam at the surface of the skin is preferably on the order of, and preferably much greater than, the depth of the target to be irradiated. Most preferably, the beam diameter is at least 8 mm. The area of the irradiating field is preferably between about 0.5 and 2 cm$^2$, and is most preferably between 0.75 and 1 cm$^2$. Because the beam is preferably converged, the spatial profile will be condensed as a function of depth before reaching a waist at a depth defined by optical scattering in the dermis. Preferably, as shown in FIG. 5B, the intensity across the beam diameter is roughly constant in order to provide a substantially uniform irradiating field.

Figure 6:
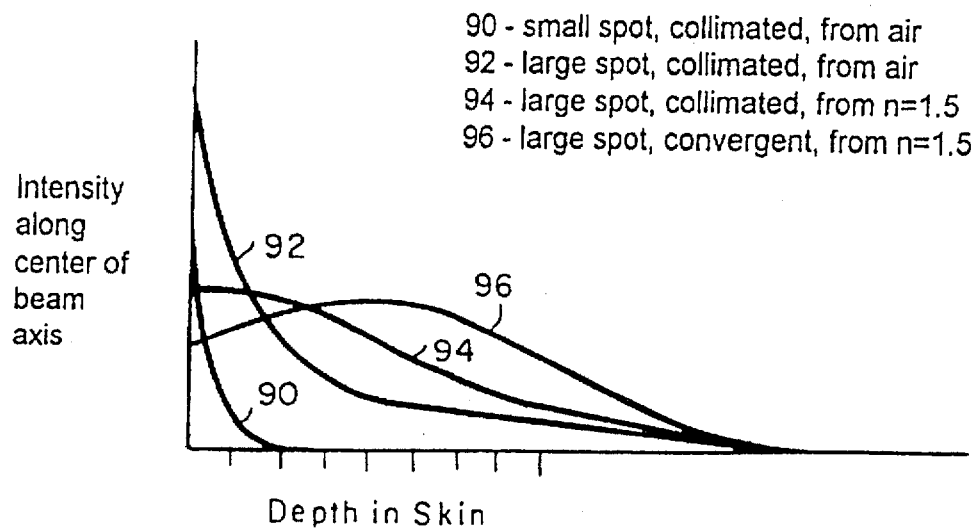
FIG. 6 is a plot of the computer-generated optical intensity as a function of skin depth for different optical fields.

Referring now to FIG. 6, following illumination, the intensity distribution of optical radiation (i.e., the y axis in the figure) as a function of skin depth (i.e., the x axis) is calculated using Monte Carlo-based computer simulations. The distribution is a function of the beam's spatial profile, the optical properties of the medium in contact with the skin. Although the plotted data is based on a computer simulation, and is thus only an approximate, the x axis units are estimated to be about 500 microns per tick mark. The first curve 90 shows the skin depth-dependent properties of an optical field originating from a small, collimated spot of 800 nm light in air. In this case, the majority of the optical intensity is distributed near the surface of the skin (indicated by the "0" point along the x axis), with the intensity dropping off rapidly at larger depths. A larger, collimated spot originating from air (curve 92) has a more evenly distributed skin depth-dependent intensity, although the majority of the light is still concentrated near the skin surface. Delivering a large, collimated radiation spot from a material having a refractive index of 1.5 (curve 94) results in a relatively uniform optical intensity in the first millimeter or so of the skin; at larger depths, this intensity starts to tail off with a relatively slow time constant. Finally, in the preferred embodiment, a large, spatially converging optical field from the n=1.5 refracting material has an intensity at the skin surface which increases to a maximum after propagating about a millimeter into the skin. The intensity then attenuates as a function of skin depth with a time constant slower than that exhibited by the curve 94. Thus, a field of this type can be used to effectively heat the target sites of the follicle, with reduced heating of the skin at the surface, thus reducing heat injury to the skin.

In the case where the illuminating laser generates a beam having a diameter less than the preferred values, it may be necessary to expand the beam prior to delivery to the irradiating unit. This may be done with conventional telescoping optics, e.g., two-lens systems configured to first expand and then collimate the emitted beam. Alternatively, as shown in FIG. 2A, the irradiating field may be coupled into an optical fiber and then delivered to the irradiating unit. In this case, the emerging field is naturally dispersed due to the waveguide nature of the fiber, and is then collected by a collimating lens. Displacement of the lens from the fiber tip allows the irradiating beam's profile to be increased to the desired amount.

The fluence of the optical field will be varied according to the degree of pigmentation in the patient, and is preferably between about 10 and 200 J/cm$^2$ for each pulse; patients with darker hair will require lower fluence than patients with lighter hair. Most preferably, the pulse fluence of the irradiating field for pulses of about 1 ms duration is between 30 and 50 J/cm$^2$. As described herein, in all cases, the fluence is adjusted in order to heat the target regions to the desired temperature of approximately 80° to 120° C. Moreover, the level of fluence may be increased as the pulse duration is increased in order to compensate for less efficient heating of follicles due to heat conduction during long pulses. It may be necessary to increase or decrease the optical fluence in order to heat the hair follicle to the desired temperature if the wavelength of the irradiating light field does not lie in the preferred spectral regions (i.e., 680–900 nm or 1000–1200 nm). In addition, in cases where the laser output is below the desired optical fluence, it may be necessary to amplify the individual pulses prior to irradiating the skin. Optical amplifiers, such as external optical cavities, may be used for this purpose.

Table 1, shown below, lists the preferred parameters of the optical fields used for hair removal. The value of each parameter depends on the amount of hair in the region of interest, the degree of pigmentation of the hairs, and the pigmentation of the surrounding skin of the patient.

TABLE 1

Preferred Optical Field Parameters

| Parameter | Range | Preferred Values |
|---|---|---|
| Wavelength | 680–1200 nm | 680–900, 1000–1200 nm |
| Pulse Duration | 50 μs–200 ms | 2–100 ms |
| Beam Area | >0.5 cm$^2$ | 0.75–1.0 cm$^2$ |
| Pulse Energy | 10–200 J/cm$^2$ | 30–50 J/cm$^2$ |
| Optical Coupling | external n ≧ 1.4 | n = 1.5 to 1.7 |
| Beam Convergence, At Skin Surface | collimated or convergent | f# 0.5–2 |

The inventions will now be further described with reference to the following examples.

EXAMPLES

In order to demonstrate the efficacy of the hair-removal device according to the invention, in vitro black-haired dog skin was exposed to light from the normal mode of a ruby laser at λ=694 nm with a pulse duration of 270μs and optical fluences of 40 J/cm$^2$, 71 J/cm$^2$, and 160 J/cm$^2$. The spatial extent of the beam (8 mm diameter at the skin surface) allowed irradiation of approximately 100 hairs with a single laser shot. Following irradiation, each skin region was examined histologically. Examination revealed that at the highest fluences, dermal damage consistent with scarring of the skin was evident, indicating that at the highest fluences, light-induced thermal damage was not selective to the hairs. In contrast, at the lower fluences, and particularly at 40 J/cm$^2$, localized follicular damage was observed, with no noticeable damage occurring in the neighboring skin regions or dermis between hair follicles.

In a separate set of experiments, in order to show that the temperature increase within the irradiated hair is dependent on the degree of pigmentation, fresh human hair and skin samples having different colors were exposed using the hair-removal method described herein. The light source for all experiments was the ruby laser described above. Emitted light was first coupled into an enclosed beam-steering device containing several mirrors coated to have high reflectivities at 694 nm, and then delivered to an irradiating unit similar to that shown in FIG. 2B. The unit included a 5-cm plano-convex glass lens positioned at the proximal end of a water-cooled plexiglass housing. A sapphire contact device shaped as a 1-cm focal length lens was disposed at the distal end of the contact device, with the convex side touching the skin to allow compression during exposure as described above. Human skin was irradiated with an 8 mm diameter beam by pressing the cooled (4° C.) contact device against the skin region of the patients, and then delivering a single laser shot. Each shot typically resulted in the simultaneous exposure of about 10 hairs.

Figure 7:
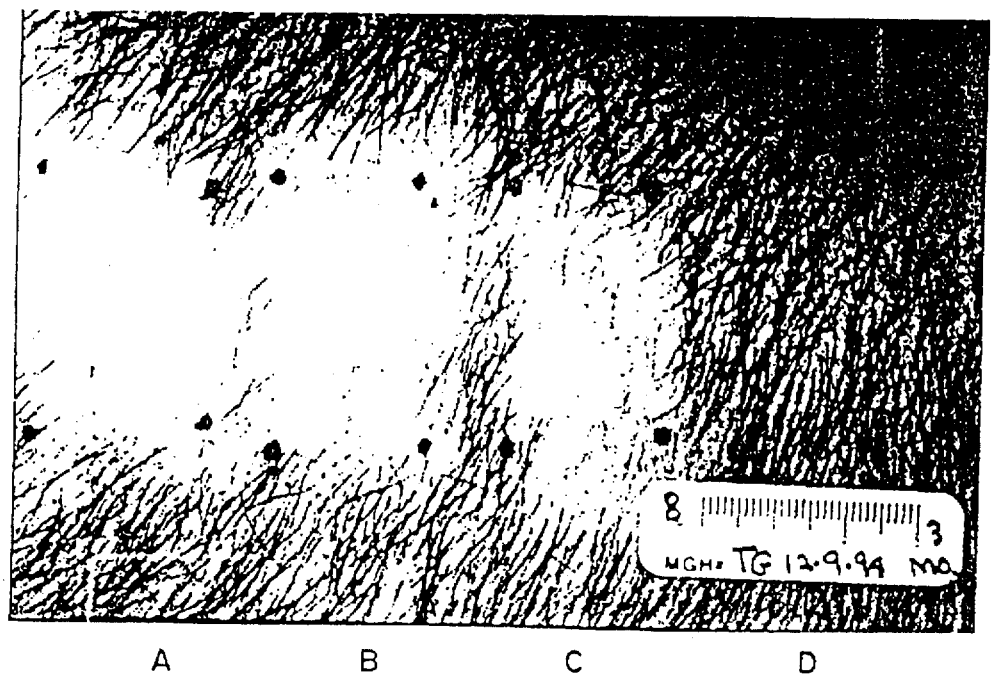
FIG. 7 is a photograph showing skin regions of a patient three months after being treated according to the hair removal method of the invention.

The skin and hair of six adult patients having hair color ranging from red to black was irradiated and then observed. In each patient, eight treatment sites, each having an area of 10 cm$^2$, were irradiated. In order to monitor destruction of the papilla, sites 1–4 were wax-epilated prior to exposure to laser light, while sites 5–8 were shaven prior to exposure. Each site then received an optical fluence of either 28 J/cm$^2$, 42 J/cm$^2$, or 57 J/cm$^2$. Patients were seen in follow-up examinations one month and three months (and for some patients also one year) after exposure. As seen from the photographs of the exposed regions shown in FIG. 7 (i.e., regions A–C), hair regrowth after three months was minimal or non-existing in all cases compared to the shaved-but-untreated region (Region D), clearly indicating permanent damage to the hair follicle. In the figure, sites A–C were treated with decreasing energy from the laser. It is clearly evident that hair removal is relatively less pronounced in region C, treated with a fluence of 27 J/cm$^2$. Region D, the control region, was shaven at the same day regions A–C were treated. In addition, histological specimens obtained from the treated sites revealed that damage occurred exclusively to the hair follicle, while the surrounding dermis was essentially spared. There was statistically significant loss of hair for all of the subjects in the laser-treated sites compared with unexposed, shaven control sites. At one year later, there was also significant permanent hair loss without any scarring.

A separate set of experiments permitting measurement of the time-dependent temperature characteristics of hair and skin samples were conducted using a pulsed photothermal radiometry (PPTR) apparatus. In these experiments, the ruby laser described above was used at lower fluences to provide optical pulses having an energy allowing heating, but not destruction, of the follicles. Output from the laser was focussed onto the samples of human hair and skin to provide a uniform excitation field. A New England Research, Inc. black-body radiation detector containing an amplified, liquid nitrogen-cooled HgCdTe detector was used to monitor time-dependent characteristics of the sample temperature, and a Gentec, Inc. laser energy meter was used to monitor the irradiating pulse. The output from both detectors was then amplified with a compensated 0–10 Mhz dc-coupled preamplifier, and then relayed to a digital oscilloscope for recording and storing the data.

Eight patients having various skin types and hair coloring ranging from red/blonde to black were studied. In general, the PPTR results indicated that following irradiation at 694 nm, black hair experienced a larger temperature rise than lighter brown hair, and that both of these specimens experienced higher temperature rises compared to red/blonde hair. In addition, following irradiation, type II skin had a lower temperature rise than type III or type IV skin.

Figure 8A:
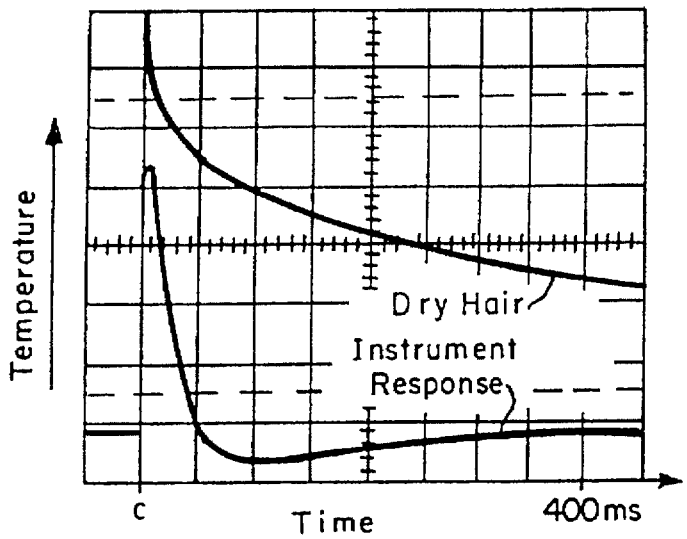
FIGS. 8A, 8B and 8C are oscilloscope traces showing, following irradiation, the time-dependent temperature responses of, respectively, dry black hair, wet black hair, and live skin surrounding the black hair sample.
Figure 8B:
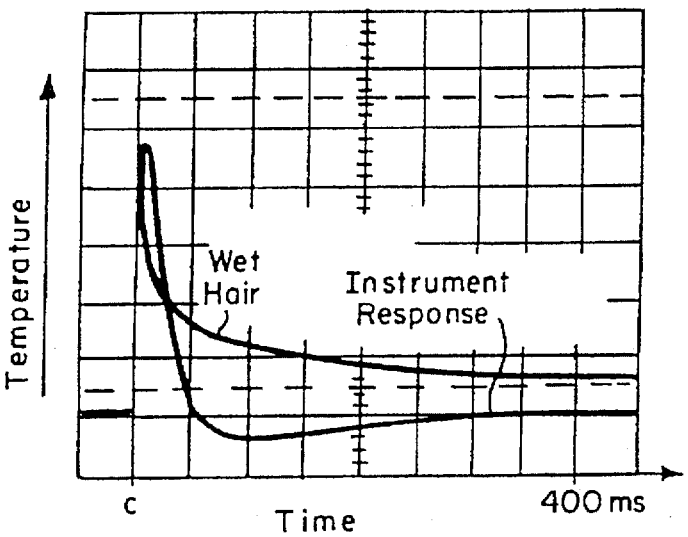
Figure 8C:
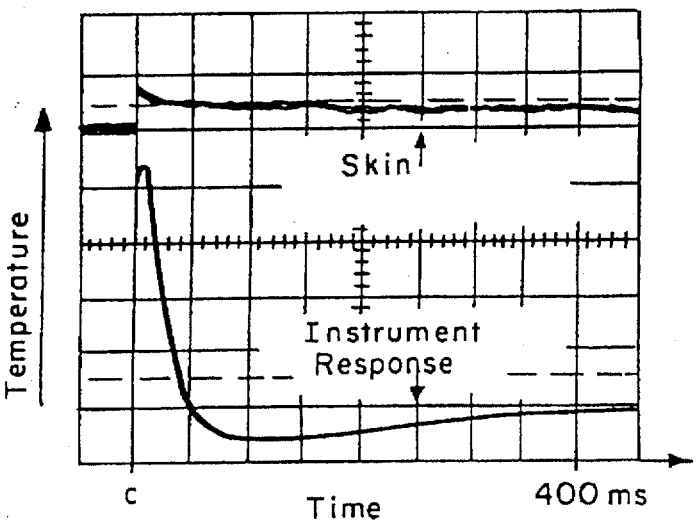

Referring now to FIGS. 8A–8C, in a particular example using a patient with black hair and white skin, time-dependent traces measured using the PPTR apparatus indicate that 400 ms after irradiation, both wet and dry black hair experience, respectively, temperature rises of about 7° C. and 72° C. (FIGS. 8A and 8B) from a baseline temperature of 23 ° C., whereas the surrounding skin (FIG. 8C) undergoes a temperature rise of less than 1° C. The difference in the temperature rise and time-dependent decay characteristics of the wet hair is likely due thermal effects (e.g., the higher heat capacity of wet hair).

Figure 9:
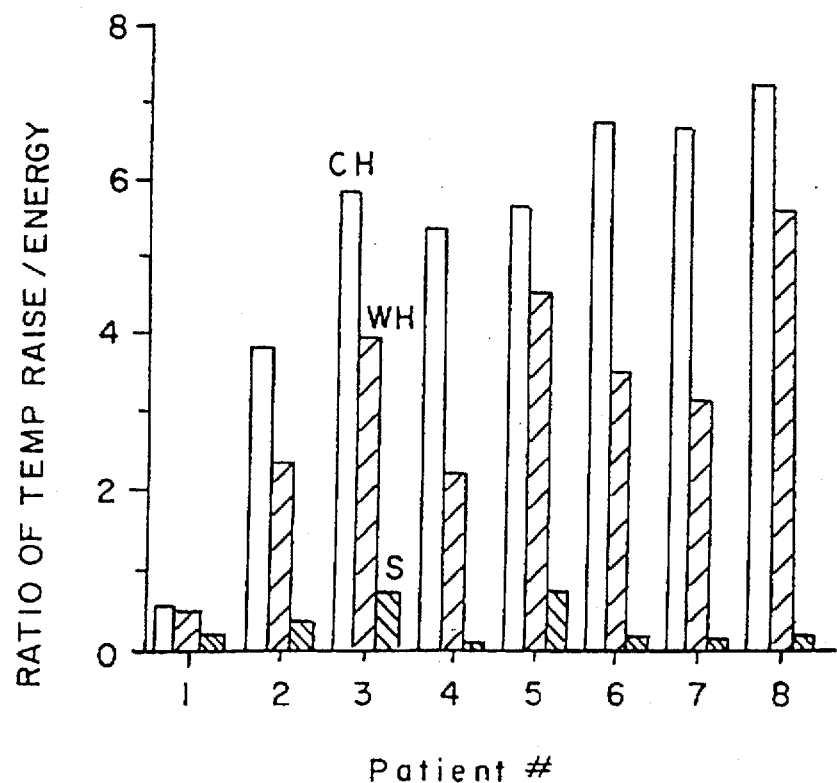
FIG. 9 is a plot showing the temperature rise as a function of laser pulse energy for dry hair (DH), wet hair (WH), and skin (S) samples of eight different patients.

Referring now to FIG. 9, in all cases, the normalized temperature rises (i.e, the ratio of temperature rise to laser pulse energy) in the wet and dry hair follicles were significantly higher than those measured in the skin, indicating selective heating of the follicles using the method of the invention. Table 2, shown below, lists the hair and skin types of each patient in the study. The patient numbers in the table correspond to the patient numbers in FIG. 9.

TABLE 2

Patient Hair and Skin Types

| Patient | Hair | Skin Type |
|---------|------|-----------|
| 1 | Red | II |
| 2 | Brown | III |
| 3 | Brown | II |
| 4 | Gray/Black | III |
| 5 | Gray/Black | III |
| 6 | Dark Brown | III |
| 7 | Gray/Black | II |
| 8 | Black | III |

OTHER EMBODIMENTS

Figure 10A:
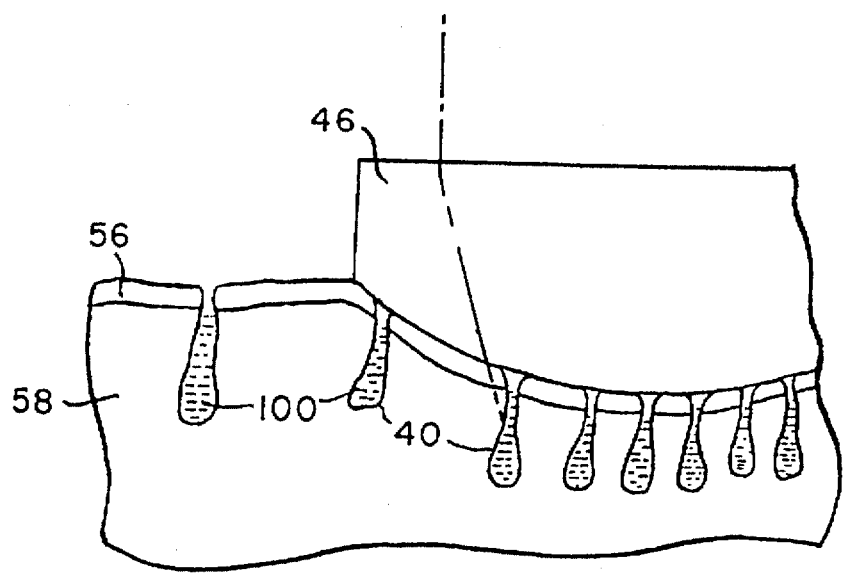
FIG. 10A is a partial cross-sectional view of the applicator of the invention being used to practice an alternative embodiment of the invention wherein epilation and filling of empty follicles with a chromophore performed before irradiation.

FIG. 10A illustrates an alternative embodiment of the invention wherein the region 20 is epilated rather than being merely shaved prior to treatment in accordance with the teachings of this invention. A fluid solution or suspension 100 containing a chromophore may then be applied to the skin region 20, with the chromophore containing fluid migrating into the empty follicles and filling the follicles. "Capillary action" of the fluid/chromophore into the follicles is desirable and may be enhanced by providing a low surface tension between the fluid and skin, for example by using surfactants or solvents. The excess fluid/chromophore may then be removed from the skin surface by washing, wiping or stripping. During irradiation, the chromophore 100 in the follicle absorbs light and is heated and, along with the heating of the melanin of the follicle itself, results in significant heating of the follicle to destroy the portions thereof, including the bulge and the papilla, required to prevent regrowth of hair. The chromophore therefore must absorb light at the wavelength or wavelengths used for irradiation. Suitable chromophores might include a carbon particle suspension or a dye such as methylene blue or indocyanine green. Melanin itself in liposomal form might also be used. Since the chromophore is only in the follicles, this technique maximizes damage to the follicles while minimizing damage to surrounding tissue, and for this reason is a preferred way of practicing the invention, especially for those with blond, red, light brown or other light colored hair. Except for the differences indicated above, this embodiment of the invention operates in the same manner described for earlier embodiments, including the cooling of contact device 46, the deformation of the skin in the region 20, and the preferred optical irradiation, with the exception that lower frequency may be allowed when using the chromophores.

Figure 10B:
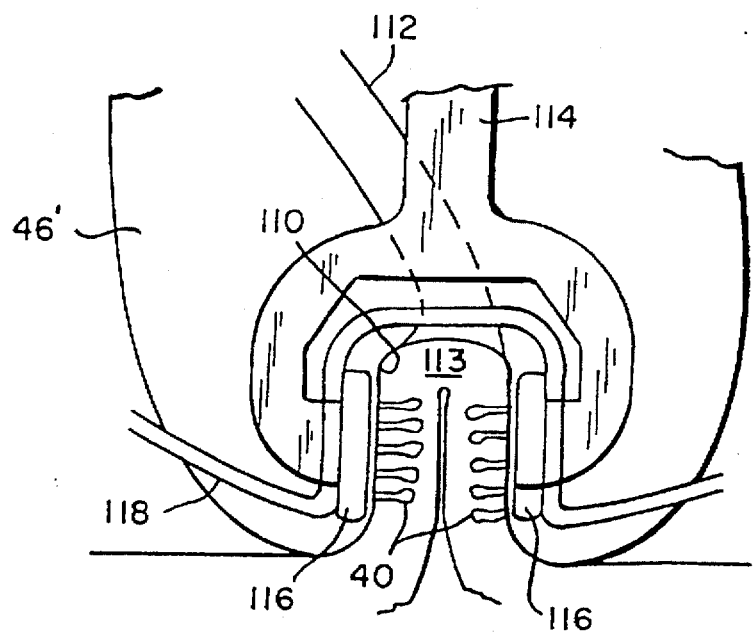
FIG. 10B is a cross-sectional view of an applicator for an alternative embodiment being used for hair removal.

FIG. 10B illustrates another alternative embodiment of the invention wherein the contact device or applicator 46' is modified so as to simultaneously expose both sides of a skin fold. This further increases the relative delivery of light to the deep portion of the follicles. In FIG. 10B, the contact device has for example an opening or slot 110 in the face of the applicator into which the area 20 of the skin may be drawn by for example vacuum or suction being applied to line 112 leading into the top of slot 110, the skin in slot 110 being formed into a fold 113. Radiation may be applied through a fiber-optic bundle 114 which divides to apply the radiation to lenses 116 on either side of slot 110. Cooling water may be flowed over the surfaces of lenses 116 through a line 118. Alternatively, two applicators similar to those shown for example in FIG. 2A or 2B can be positioned on opposite sides of a skin fold formed by clamping the skin region therebetween or by other suitable means.

The advantage of folding the skin as discussed for the above embodiments is that radiation is applied to a relatively thin section of skin from both sides. Thus, the papilla of a given follicle may be receiving radiation not only from the lens 116 on the side of slot 110 where the follicle is located, but also some radiation from the lens 116 on the opposite sides of the slot. Thus, energy applied to the papilla of each follicle is increased without increasing the energy at the surface, thus facilitating hair removal with less pain and injury. By making the slot 110 relatively narrow, pressure is applied to the skin on both sides of the slot, the skin being compressed between the walls of the slot. The advantages of compressing the skin, including removing blood therefrom and reducing the distance from the skin surface to the papilla, are thus also achieved by this embodiment of the invention. Clamping to form the fold would also apply pressure to the skin.

It may also be possible to utilize the teachings of this invention for short term hair removal, the device serving as for example a razor which might provide a shave lasting for perhaps one to two weeks. This is achieved by applying the fluid/chromophore to the region which is to be "shaved" which region has preferably been shaved using conventional techniques, but not epilated. In this case the chromophore can only migrate a few millimeters into the follicle, to for example the level of the sebaceous gland. Excess chromophore may then be removed, and the contact device of this invention utilized with relatively low level radiation to heat the chromophore, and destroy the hair surrounded thereby, without substantial damage to either the skin or follicle.

Further, while cooling water has been shown for the preferred embodiment to cool contact device 46, this is not a limitation on the invention and other cooling techniques may be utilized. For example, a low temperature gas or liquid gas may be passed over the contact device for cooling purposes or the contact device may be sufficiently cooled prior to use so that it can continue to perform the cooling function during irradiation without having a cooling medium passed thereover. Other cooling techniques known in the art may also be utilized.

Other embodiments are within the scope of the following claims. For example, the contact device may not be cooled or cooling of the epidermis may be performed without an applicator (for example cryogenically). Where an applicator is not utilized, radiation is applied directly to the region of interest after passing through the appropriate optics.

Thus, while the invention has been particularly shown and described above with reference to preferred embodiments, the foregoing and other changes in form and detail may be made therein by one skilled in the art without departing from the spirit and scope of the invention.

We claim:

1. A method for the simultaneous removal of a plurality of hairs from a skin region, each hair being in a follicle extending into the skin from a skin surface, the method comprising the steps of:
   (a) placing an applicator in contact with the skin surface in said skin region;
   (b) applying optical radiation of a selected wavelength and of a selected fluence through said applicator to said skin region, said applying step lasting for a predetermined time interval; and
   (c) utilizing said applicator at least during step (b) to cool the skin surface in said skin region to a selected depth; said selected fluence and said predetermined time interval being selected such that there is at most minimal heating of skin in said skin region to said selected depth, while causing sufficient heating of at least one of hairs and follicles below said selected depth to at least damage said hairs and follicles without causing significant damage to tissue surrounding said follicles.

2. A method as claimed in claim 1 wherein the skin has an epidermis layer which is the layer of the skin closest to said skin surface, and wherein said selected depth is substantially the depth of said epidermis layer.

3. A method as claimed in claim 1 wherein step (c) includes the step of (d) cooling at least the surface of said applicator in contact with said skin surface both during step (b) and prior to the performance thereof.

4. A method as claimed in claim 3 wherein step (d) is performed by passing a cooling fluid through said applicator.

5. A method as claimed in claim 3 wherein step (b) is not performed until the skin surface in said skin region has been cooled to substantially said selected depth.

6. A method as claimed in claim 1 wherein said selected fluence and said predetermined time interval are such as to result in the substantial destruction of said follicles.

7. A method as claimed in claim 1 wherein said selected time interval is 2 to 100 ms.

8. A method as claimed in claim 1 including the step performed before step (a) of shaving the hairs in said skin region.

9. A method as claimed in claim 1 including the step performed before step (a) of epilating the hairs in said skin region.

10. A method as claimed in claim 9 including the step performed after the epilating step but before step (a) of filling the follicles from which the hairs have been epilated with a substance which preferentially absorbs optical radiation at said selected wavelength.

11. A method for the simultaneous removal of a plurality of hairs from a skin region, each hair being in a follicle extending into the skin from a skin surface, the method comprising the steps of:
   (a) placing an applicator in contact with the skin surface in said skin region; and
   (b) applying optical radiation of a selected wavelength and of a selected fluence through said applicator to said skin region, said applying step lasting for a predetermined time interval;
said applicator converging the optical radiation applied to said skin region.

12. A method for the simultaneous removal of a plurality of hairs from a skin region, each hair being in a follicle extending into the skin from a skin surface, the method comprising the steps of:
   (a) placing an applicator in contact with the skin surface in said skin region; and
   (b) applying optical radiation of a selected wavelength and of a selected fluence through said applicator to said skin region, said applying step lasting for a predetermined time interval;
pressure being applied to the applicator during steps (a) and (b) so as to cause the applicator to deform the skin region thereunder.

13. A method as claimed in claim 12 wherein the applicator has a convex surface in contact with the skin surface.

14. A method as claimed in claim 12 wherein the pressure applied to said applicator is greater than blood pressure of a patient from whom hairs are being removed, whereby at least some blood is removed from said skin region.

15. A method for the simultaneous removal of a plurality of hairs from a skin region, each hair being in a follicle extending into the skin from a skin surface, the method comprising the steps of:

(a) utilizing an applicator to form a fold of the skin in said skin region, said applicator being in contact with the skin surface in said skin region on two substantially opposite sides of said fold; and (b) applying optical radiation of a selected wavelength and of a selected fluence through said applicator to said skin region, said applying step lasting for a predetermined time interval, the optical radiation being applied to said two substantially opposite sides of the fold.

16. A method as claimed in claim 15 wherein the applicator has a slot formed in the surface thereof in contact with the skin surface, wherein during step (a) at least a portion of the skin region is drawn up into said slot, and wherein during step (b) optical radiation is applied to the skin region from at least two opposite sides of said slot.

17. A method for the simultaneous removal of a plurality of hairs from a skin region, each hair being in a follicle extending into the skin from a skin surface, the method comprising the steps of:

(a) placing an applicator in contact with the skin surface in said skin region, said step including the step of providing a substantial refractive index match between the applicator and the skin surface in said skin region; and (b) applying optical radiation of a selected wavelength and of a selected fluence through said applicator to said skin region, said applying step lasting for a predetermined time interval.

18. A method as claimed in claim 17 wherein step (e) includes the step of providing a layer of a refractive index matching substance between the applicator and the skin surface in said skin region.

19. A method for the simultaneous removal of a plurality of hairs from a skin region, each hair being in a follicle extending into the skin from a skin surface, the method comprising the steps of:

(a) applying optical radiation of a selected wavelength and of a selected fluence to said skin region, said applying step lasting for a predetermined time interval; and (b) cooling the skin surface in said skin region to a selected depth prior to step (a) and during step (a), said selected fluence and said predetermined time interval being selected such that there is at most minimal heating of skin in said skin region to said selected depth, while causing sufficient heating of at least one of hairs and follicles below said selected depth to at least damage said hairs and follicles without causing significant damage to tissue surrounding said follicles;

whereby at least one of the hairs and follicles is heated and damaged without causing significant damage to the skin surface in said skin region up to said selected depth.

20. A method as claimed in claim 19 wherein said selected depth is substantially the entire epidermal layer depth in said region, but does not extend significantly into the dermal layer.

21. An applicator suitable for use in practicing the method of claim 1 comprising:

a housing;

a transmitter of optical radiation into said housing;

a surface disposed on the housing having a convex shape and adapted to be in pressure contact with the skin surface in said skin region;

an optical path from said inlet to through said housing from said transmitter of optical radiation to optical radiation at said selected wavelength;

an element in said optical path for converging the optical radiation as it leaves the applicator through said surface; and means for cooling said surface to a temperature below that of the skin region.

22. An applicator as claimed in claim 21 wherein at least said surface is formed of a material having a refractive index which substantially matches, but which is not less than, the refractive index of the skin surface in said skin region.

23. An applicator as claimed in claim 21 wherein said element is a lens.

24. An applicator as claimed in claim 21 wherein said means for cooling is a channel near said surface through which cooling water is passed.

25. An applicator suitable for use in practicing the method of claim 1 comprising:

a housing;

a transmitter of optical radiation into said housing;

a surface disposed on the housing shaped to contact the skin surface in said skin region, said surface having a slot formed therein;

an optical path from said inlet to through said housing from said transmitter of optical radiation to optical radiation at said selected wavelength, said optical path leading to at least two opposite sides of said slot, and including means for positioning at least a portion of said skin region into said slot;

an element in said optical path for converging the optical radiation as it leaves the applicator through said surface; and means for cooling said surface to a temperature below that of the skin region.

26. An applicator as claimed in claim 25 wherein said means for positioning includes means for applying vacuum to said slot.

27. Apparatus for the simultaneous removal of a plurality of hairs from a skin region containing said plurality of hairs, each hair being in a follicle extending into the skin from a skin surface, the apparatus comprising:

an applicator which is adapted to be in pressure contact with a portion of the skin surface containing a plurality of hairs in said skin region;

a source of optical radiation of a wavelength between 680 and 1,200 nm, a fluence between 10 and 200 J/cm$^2$ and a pulse duration between 50µs and 200 ms; and means for applying the optical radiation from said source to said applicator, the optical radiation being passed through the applicator to said skin region.

28. Apparatus as claimed in claim 27 wherein said applicator has a surface in contact with the skin surface, and including a mechanism which cools said surface of the applicator below that of the skin region by an amount which is sufficient in conjunction with selected radiation to prevent substantial heating of the skin region in which said applicator is in pressure contract for a selected depth and not to substantially interfere with heating of the skin in said region beyond said selected depth.

29. Apparatus as claimed in claim 28 wherein said means for cooling includes a channel near said surface through which cooling water is passed.

30. Apparatus as claimed in claim 28 wherein said source of optical radiation is a laser, and wherein said selected duration is 2 to 100 ms.

31. Apparatus as claimed in claim 27 wherein said applicator has a surface in contact with said skin surface, said surface of the applicator having a slot formed therein, wherein the means for applying the optical radiation includes optical paths in said applicator leading to at least two opposite sides of said slot, and wherein said applicator includes means for positioning at least a portion of said skin region in said slot between said at least two opposites sides.

32. A method for the simultaneous removal of a plurality of hairs from a skin region, each hair being in a follicle extending into the skin from a skin surface, the method comprising the step of:

(a) positioning an element over said skin surface in said skin region through which optical radiation may be passed; and (b) applying optical radiation of a selected wavelength and of a selected fluence through said element to said skin region to simultaneously remove a plurality of hairs from said region, said applying step lasting for a duration of from 2 to 100 ms.

* * * * *

(12) EX PARTE REEXAMINATION CERTIFICATE (7214th)

United States Patent
Anderson et al.

(10) Number: US 5,735,844 C1
(45) Certificate Issued: Dec. 8, 2009

(54) HAIR REMOVAL USING OPTICAL PULSES

(75) Inventors: R. Rox Anderson, Lexington, MA (US);
Melanie Grossman, Boston, MA (US);
William Farinelli, Danvers, MA (US)

(73) Assignee: The General Hospital Corporation

Reexamination Request:
No. 90/009,216, Jul. 10, 2008
No. 90/009,356, Dec. 8, 2008

Reexamination Certificate for:
Patent No.: 5,735,844
Issued: Apr. 7, 1998
Appl. No.: 08/593,565
Filed: Jan. 30, 1996

Related U.S. Application Data

(63) Continuation-in-part of application No. 08/382,122, filed on Feb. 1, 1995, now Pat. No. 5,595,568.

(51) Int. Cl.
*A61B 18/20* (2006.01)
*A61B 17/22* (2006.01)
*A61B 17/30* (2006.01)
*A61B 18/00* (2006.01)
*A61B 18/22* (2006.01)
*A61B 19/00* (2006.01)
*A61N 5/06* (2006.01)
*A61B 17/00* (2006.01)

(52) U.S. Cl. .......................................... 606/9
(58) Field of Classification Search ................ 606/9
See application file for complete search history.

(56) References Cited

U.S. PATENT DOCUMENTS

| | | | |
|---|---|---|---|
| 2,262,215 A | 11/1941 | Bird | |
| 3,404,350 A | 10/1968 | Muncheryan | |
| 3,538,919 A | 11/1970 | Meyer | |
| 3,583,919 A | 6/1971 | Meyer | |
| 3,693,623 A | 9/1972 | Harte et al. | |
| 3,821,510 A | 6/1974 | Muncheryan | |
| 3,834,391 A | 9/1974 | Block | |
| 3,900,034 A | 8/1975 | Katz et al. | |
| 3,916,143 A | 10/1975 | Farrell | |
| 4,140,130 A | 2/1979 | Storm, III | |

(Continued)

FOREIGN PATENT DOCUMENTS

| | | |
|---|---|---|
| CA | 2210720 | 8/1996 |
| CN | 86201325 U | 11/1987 |
| DE | 3220962 | 12/1983 |
| DE | 4304091 | 8/1994 |
| DE | 19512481 | 10/1995 |

(Continued)

OTHER PUBLICATIONS

Goldman, "Surgery by Laser for Malignant Melanoma", J. Dermatol. Surg. Oncol., 5(2):141–144 (1979).
Goldman, *Biomedical Aspects of the Laser,* Springer–Verlag, pp. iii–11 and 220–232 (1967).
Goldman, et al., "Laser Action at the Cellular Level", JAMA, 198:641–644 (1966).

(Continued)

*Primary Examiner*—David O. Reip

(57) ABSTRACT

A method and apparatus for simultaneously effecting the removal of multiple hairs from a skin region by using light energy to destroy hair follicles in the region. Light energy is applied to the region through an applicator which converges the light energy to enhance destruction of desired portions of the follicles, is preferably pressed against the skin region to deform the upper layers of the skin reducing the distance from the skin surface to portions of hair follicles which are to be destroyed, including the bulge and papilla of the follicles, and which applicator is preferably cooled to minimize or eliminate thermal damage to the epidermis in the region being irradiated. Parameters for the irradiation, including pulse duration, are selected to effect complete damage of desired portions of the hair follicles in the region with minimal damage to surrounding tissue and to the patient's epidermis.

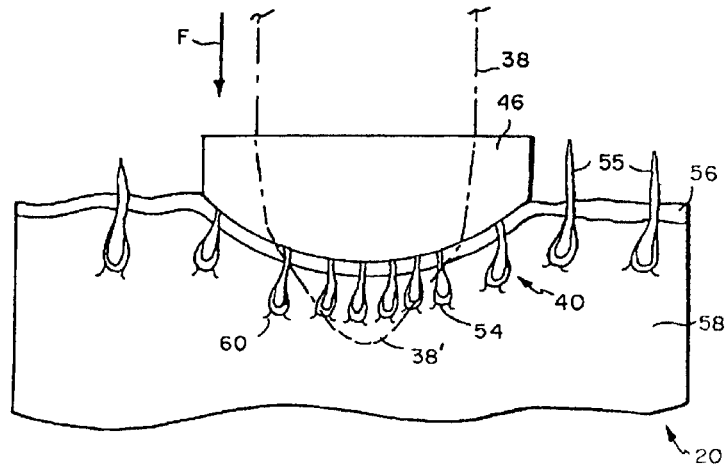

U.S. PATENT DOCUMENTS

| | | | |
|---|---|---|---|
| 4,174,713 A | 11/1979 | Mehl | |
| 4,174,714 A | 11/1979 | Mehl | |
| 4,388,924 A | 6/1983 | Weissman et al. | |
| 4,461,294 A | 7/1984 | Baron | |
| 4,566,454 A | 1/1986 | Mehl et al. | |
| 4,608,978 A | 9/1986 | Rohr | |
| 4,617,926 A | 10/1986 | Sutton et al. | |
| 4,718,416 A | 1/1988 | Nanaumi et al. | |
| 4,733,660 A | 3/1988 | Itzkan | |
| 4,819,669 A | 4/1989 | Politzer et al. | |
| 4,829,262 A | 5/1989 | Furumoto | |
| 4,930,504 A | 6/1990 | Diamantopoulos et al. | |
| 5,000,752 A | 3/1991 | Hoskin et al. | |
| 5,057,104 A | 10/1991 | Chess | |
| 5,059,192 A | 10/1991 | Zaias | |
| 5,065,515 A | 11/1991 | Iderosa | |
| 5,139,495 A | 8/1992 | Daikuzono et al. | |
| 5,182,857 A | 2/1993 | Simon et al. | |
| 5,217,455 A | 6/1993 | Tan | |
| 5,226,907 A | 7/1993 | Tankovich | |
| 5,282,797 A | 2/1994 | Chess | |
| 5,290,273 A | 3/1994 | Tan | |
| 5,290,274 A | 3/1994 | Levy et al. | |
| 5,299,104 A | 3/1994 | Parmentier | |
| 5,299,453 A | 4/1994 | Sprunt et al. | |
| 5,304,170 A | 4/1994 | Green | |
| 5,312,395 A | 5/1994 | Tan et al. | |
| 5,320,618 A | 6/1994 | Gustafsson et al. | |
| 5,337,741 A | 8/1994 | Diamond | |
| 5,344,418 A | 9/1994 | Ghaffari | |
| 5,397,327 A | 3/1995 | Koop et al. | |
| 5,405,368 A | 4/1995 | Eckhouse et al. | |
| 5,425,728 A | 6/1995 | Tankovich | |
| 5,464,436 A | 11/1995 | Smith | |
| 5,474,549 A | 12/1995 | Ortiz et al. | |
| 5,486,172 A | 1/1996 | Chess | |
| 5,522,813 A | 6/1996 | Trelles et al. | |
| 5,527,350 A | 6/1996 | Grove et al. | |
| 5,546,214 A | 8/1996 | Black et al. | |
| 5,554,156 A | 9/1996 | Shimizu et al. | |
| 5,586,981 A | 12/1996 | Hu | |
| 5,595,568 A | 1/1997 | Anderson et al. | |
| 5,606,798 A | 3/1997 | Kelman et al. | |
| 5,620,478 A | 4/1997 | Eckhouse et al. | |
| 5,630,811 A | 5/1997 | Miller | |
| 5,647,866 A | 7/1997 | Zaias et al. | |
| 5,653,706 A | 8/1997 | Zavislan et al. | |
| 5,683,380 A | 11/1997 | Eckhouse et al. | |
| 5,707,403 A | 1/1998 | Grove et al. | |
| 5,735,844 A | 4/1998 | Anderson et al. | |
| 5,752,948 A | 5/1998 | Tankovich et al. | |
| 5,757,949 A | 5/1998 | Kinoshita et al. | |
| 5,766,214 A | 6/1998 | Mehl, Sr. et al. | |
| 5,814,040 A | 9/1998 | Nelson et al. | |
| 5,817,089 A | 10/1998 | Tankovich et al. | |
| 5,820,625 A | 10/1998 | Izawa et al. | |
| 5,824,023 A | 10/1998 | Anderson | |
| 5,836,938 A | 11/1998 | Slatkine et al. | |
| 5,846,252 A | 12/1998 | Mehl, Sr. | |
| 5,853,407 A | 12/1998 | Miller | |
| 5,860,967 A | 1/1999 | Zavislan et al. | |
| 5,868,732 A | 2/1999 | Waldman et al. | |
| 5,871,479 A | 2/1999 | Furumoto et al. | |
| 5,879,346 A | 3/1999 | Waldman et al. | |
| 5,885,273 A | 3/1999 | Eckhouse et al. | |
| 5,906,610 A | 5/1999 | Mehl, Sr. et al. | |
| 5,916,211 A | 6/1999 | Quon et al. | |
| 5,925,035 A | 7/1999 | Tankovich | |
| 5,989,267 A | 11/1999 | Anderson | |
| 6,015,404 A | 1/2000 | Altshuler et al. | |
| 6,036,684 A | 3/2000 | Tankovich et al. | |
| 6,045,548 A | 4/2000 | Furumoto et al. | |
| 6,050,990 A | 4/2000 | Tankovich et al. | |
| 6,063,074 A | 5/2000 | Tankovich | |
| 6,063,076 A | 5/2000 | Mehl, Sr. et al. | |
| 6,080,147 A | 6/2000 | Tobinick | |
| 6,090,101 A | 7/2000 | Quon et al. | |
| 6,143,287 A | 11/2000 | Ben-Hur et al. | |
| 6,149,644 A | 11/2000 | Xie | |
| 6,149,645 A | 11/2000 | Tobinick | |
| 6,152,917 A | 11/2000 | Tankovich | |
| 6,165,171 A | 12/2000 | Tobinick | |
| 6,168,589 B1 | 1/2001 | Tobinick | |
| 6,168,590 B1 | 1/2001 | Neev | |
| 6,210,402 B1 | 4/2001 | Olsen et al. | |
| 6,214,034 B1 | 4/2001 | Azar et al. | |
| 6,217,572 B1 | 4/2001 | Tobinick | |
| 6,228,075 B1 | 5/2001 | Furumoto | |
| 6,228,078 B1 | 5/2001 | Eggers et al. | |
| 6,235,015 B1 | 5/2001 | Mead, III et al. | |
| 6,248,102 B1 | 6/2001 | Stewart | |
| 6,267,755 B1 | 7/2001 | Clementi et al. | |
| 6,267,771 B1 | 7/2001 | Tankovich et al. | |
| 6,273,883 B1 | 8/2001 | Furumoto | |
| 6,273,884 B1 | 8/2001 | Altshuler et al. | |
| 6,277,111 B1 | 8/2001 | Clement et al. | |
| 6,280,438 B1 | 8/2001 | Eckhouse et al. | |
| 6,283,956 B1 | 9/2001 | McDaniel | |
| 6,287,549 B1 | 9/2001 | Sumian et al. | |
| 6,365,145 B1 | 4/2002 | Ben-Hur et al. | |
| 6,383,176 B1 | 5/2002 | Connors et al. | |
| 6,485,484 B1 | 11/2002 | Connors et al. | |
| 6,508,813 B1 | 1/2003 | Altshuler | |
| 6,511,475 B1 | 1/2003 | Altshuler et al. | |
| 6,514,242 B1 | 2/2003 | Vasily et al. | |
| 6,514,243 B1 | 2/2003 | Eckhouse et al. | |
| 6,547,781 B1 | 4/2003 | Furumoto | |
| 6,595,985 B1 | 7/2003 | Tobinick | |
| 6,610,052 B2 | 8/2003 | Furumoto | |
| 6,632,218 B1 | 10/2003 | Furumoto et al. | |
| 6,706,035 B2 | 3/2004 | Cense et al. | |
| 7,029,469 B2 | 4/2006 | Vasily | |

FOREIGN PATENT DOCUMENTS

| | | |
|---|---|---|
| EP | 0142671 | 5/1985 |
| EP | 0292621 | 11/1988 |
| EP | 0565331 | 10/1993 |
| EP | 0575274 | 12/1993 |
| EP | 0 601 130 | 6/1994 |
| EP | 0 685 180 | 12/1995 |
| EP | 0736308 | 10/1996 |
| EP | 0806913 | 11/1997 |
| EP | 0893140 | 1/1999 |
| EP | 1123900 | 8/2001 |
| EP | 1219258 | 7/2002 |
| FR | 2199453 | 4/1974 |
| FR | 2590791 | 6/1987 |
| FR | 2591902 | 6/1987 |
| GB | 2123287 | 2/1984 |
| IL | 0086872 A0 | 11/1988 |
| IL | 0103728 A0 | 4/1993 |
| IL | 0097531 A0 | 12/1995 |
| JP | 64-080309 | 3/1989 |
| JP | 199574 | 4/1989 |
| JP | 1181877 | 7/1989 |
| JP | 2-13014 | 4/1990 |
| JP | 2159207 | 6/1990 |
| JP | 3123544 | 5/1991 |
| JP | 03-193003 | 8/1991 |
| JP | 3218742 | 9/1991 |
| JP | 04-067860 | 3/1992 |

| JP | 4-322668 | 11/1992 |
| JP | 5-329218 | 12/1993 |
| JP | 6509734 | 11/1994 |
| WO | WO-86/02783 | 5/1986 |
| WO | WO-89/00027 | 1/1989 |
| WO | WO-92/13684 | 8/1992 |
| WO | WO-92/16338 | 10/1992 |
| WO | WO-92/19165 | 11/1992 |
| WO | WO-93/05920 | 4/1993 |
| WO | WO-93/08715 | 5/1993 |
| WO | WO-95/15725 | 6/1995 |
| WO | WO-96/23447 | 8/1996 |
| WO | WO-96/41579 | 12/1996 |
| WO | WO-2005/016453 | 2/2005 |
| WO | WO-2006/076554 | 7/2006 |
| ZA | 9500073 A | 9/1995 |

OTHER PUBLICATIONS

Goldman, et al., "Laser Treatment of Tattoos", JAMA, 201(11): 163–166 (1967).
Goldman, et al., "Long–Term Laser Exposure of a Senile Freckle", Arch Environ Health, 22:401–403 (1971).
Goldman, et al., "Treatment of Basal Cell Epithelioma by Laser Radiation", JAMA, 189:773–775 (1964).
Margolis, et al., "Visible Action Spectrum for Melanin–Specific Selective Photothermolysis", Lasers in Surgery and Medicine, 9:389–397 (1989).
Philipp, et al., "Treatment of Congenital Vascular Disorders—Classification, Step Programme and Therapeutic Procedures", SPIE, 2086:228–238 (1993).
Seago, et al., "The Hair Cycle on the Human Thigh and Upper Arm", British Journal of Dermatology, 113:9–16 (1985).
Brief of Asclepion of Apr. 6, 2009, filed in Opposition EP 02076294.4–2305/1230900, with English Translation (7 pages).
Brief of Carl Zeiss Meditec of Apr. 9, 2009, filed in Opposition EP 96906222.3–2305/0806913, with English translation (5 pages).
Communication under Rule 51(4) EPC, Application No. 96 906 222.3–2305, dated Feb. 22, 2002 (40 pages).
Decision Revoking the European Patent EP–B–0806913 (23 pages).
Interlocutory Decision in Opposition Proceedings, Opposition 96 906 222.3–2305/806913 (37 pages).
Minutes of the Oral Proceedings before the Opposition Division, Opposition 96 906 222.3 (7 pages).
Minutes of the Oral Proceedings before the Opposition Division, Opposition EP 02 076 294.4 (8 pages).
"Summons to Attend Oral Proceedings Pursuant to Rule 71(1)EPC" issued in Opposition EP 96906222.3–1204/0806913, dated Apr. 27, 2004 (8 pages).
Interlocutory Decision in Opposition Proceedings, Opposition 02 076 294.4–2305/1230900 (39 pages).
Response to Asclepion Brief dated Apr. 6, 2009, in EP 1 230 900; Response filed Apr. 29, 2009 (4 pages).
Response to Carl Zeiss Meditec brief, dated Apr. 9, 2009, in EP 0 806 913; Response dated Apr. 29, 2009 (3 pages).
Response to Examiner's Report dated Mar. 5, 2001 in EP 96906222.3–2305; Response filed Nov. 9, 2001 (8 pages).
Response to Oppositions filed against EP 0 806 913 on Apr. 22, 2003; Response filed Dec. 19, 2003 (4 pages).
Response to Oppositions filed against EP 0 565 331; Response dated Nov. 24, 2004 (2 pages).

Anvari, et al., "A Theoretical Study of the Thermal Response of Skin to Cryogen Spray Cooling and Pulsed Laser Irradiation: Implications for Treatment of Port Wine Stain Birthmarks", Phys. Med. Biol. 40:1451–1465 (1995).
Article regarding Soviet–American Symposium on Research Technology and Trade, dated Jan. 22, 1991, Exhibit 10 to Tankovich Deposition, dated Feb. 8, 2008.
Barth, et al., "Chapter 26.1: Measurement of Hair Growth", *Handbook of Non–Invasive Methods and the Skin,* (Serup, et al., eds.), pp. 543–547 (1995).
Bartley, et al., "An Experimental Study to Compare Methods of Eyelash Ablation", Ophthalmology, 94(10):1286–1289 (1987).
Dover, et al., "Pigmented Guinea Pig Skin Irradiated With Q–Switched Ruby Laser Pulses", Arch Dermatol., 125:43–49 (1989).
Elman, et al., "Laser Assisted Hair Removal by Selective Photothermolysis—Preliminary Results".
Finkelstein, et al., "Epilation of Hair–Bearing Urethral Grafts Using the Neodymium:YAG Surgical Laser", The Journal of Urology, 146:840–842 (1991).
Gerstman, et al., "Laser Induced Bubble Formation in the Retina", Lasers in Surgery and Medicine, 18:10–21 (1996).
Goldberg, et al., "The Use of the Frequency–doubled Q–switched Nd:YAG Laser in the Treatment of Small Cutaneous Vascular Lesions", Dermatol, 22(S41):841–844.
Goldman, et al., "Effect of the Laser Beam on the Skin. III. Exposure of Cytological Preparations", J. Invest. Dermatol., 42:247–251 (1964).
Goldman, et al., "Investigative Studies with the Laser in the Treatment of Basal Cell Epitheliomas", Southern Medical Journal, 61:735–742 (1968).
Gorisch, et al., "Laser Related Heat Effects on Blood Vessels", *Lasers in Biology and Medicine,* Hillenkamp, et al., (eds.), Plenum Press, pp. 99–109, (1980).
Hair and Hair Diseases, Orfanos, et al., (eds.), Springer–Verlag (1990).
Iwasaki, et al., "Development of Laser Systems for Treatment of Hyperpigmented Skin Lesions", pp. 26–34 (1989)—English Abastract.
Iwasaki, et al., "Laser–Beam Flattening Technique and Laser Systems for Treatment of Hyperpigmented Skin Lesions", UDC—English Abstract.
Japanese Article, pp. 126–130 (1990).
Klein, et al., "Session: Biological Effects of Laser Radiation I. TAM–2: Threshold Studies and Reversible Depigmentation in Rodent Skin", NEREM Record—1965, pp. 108–109 (1965).
Konig, et al., "Fluorescence Detection and Photodynamic Activity of Endogenous Protoporphyrin in Human Skin", Optical Engineering, 31(7):1470–1474 (1992).
Kuhns, et al., "Session: Biological Effects of Laser Radiation II", Northeast Electronics Research and Engineering Meeting—NEREM, IEEE Catalogue No. F–60, pp. 152–153 (1965).
Laor, et al., "The Pathology of Laser Irradiation of the Skin and Body Wall of the Mouse", Laser Irradiation, 47(4):643663 (1965).
Merriam–Webster Online definition of Applicator.
Mester, et al., "Effect of Laser Rays on Wound Healing", American Journal of Surgery, 122:532–535 (1971).
Mester, et al., "The Stimulating Effect of Low Power Laser–Rays on Biological Systems", Laser Review, pp. 3–6, Mar. 1968.

Moretti, et al., "Laser–Based Hair Removal", A Technology/Market Study, Medical Insight, Inc. Advertisement.

Ohshiro, The Role of the Laser in Dermatology: An Atlas, Wiley, (1997).

Optical–Thermal Response of Laser–Irradiated Tissue, Welch, et al. (eds.), Plenum Press (1995).

Oxford Encyclopedic English Dictionary, p. 15 (1995).

Palomar Medical Technologies, Inc., "Medical and Technical Aspects of Laser Hair Removal", printed from http://www.thegentletouch.com/laser.med–asp.htm, printed Sep. 16, 1998.

Randall, et al., "Seasonal Changes in Human Hair Growth", British Journal of Dermatology, 124:146–151 (1991).

Saitoh, et al., "Human Hair Cycle", Journal of Investigative Dermatology, 54(1):65–81 (1970).

Stedman's Concise Medical Dictionary for the Health Professions, 4th Edition, pp. 140, 365, 890, 986 (2001).

Stedman's Medical Dictionary, 23rd Edition, pp. 203, 204 (1979).

Stedman's Medical Dictionary, 26th Edition, pp. 251–252 (1995).

Vines, "Get Under Your Skin", Inside Science, Jan., pp. 1–4 (1995).

Welch, et al., "Chapter Eighteen: Introduction to Medical Applications", *Optical–Thermal Response of Laser–Irradiated Tissue,* Welch, et al., (eds.), Plenum Press, pp. 609–618 (1995).

Welch, et al., "Chapter One: Overview of Optical and Thermal Laser–Tissue Interaction and Nomenclature", *Optical–Thermal Response of Laser–Irradiated Tissue,* Welch, et al., (eds.), Plenum Press, pp. 1–12 (1995).

Welch, et al., "Chapter Twenty–Six: Summary and Future", *Optical–Thermal Response of Laser–Irradiated Tissue,* Welch, et al. (eds.), Plenum Press, pp. 903–912 (1994).

Zeitler, et al., "Chapter 1: Laser Characteristics that Might Be Useful in Biology", Laser Applications in Medicine and Biology, vol. I, (Wolbarski, ed.), Plenum Press, pp. 1–18 (1971).

U.S. Appl. No. 08/280928, Tankovich.

File History, U.S. Appl. No. 08/280,928, entitled "Hair Removal Method", filed Jul. 26, 1994, now abandoned.

File History U.S. Pat. No. 5,683,380, entitled "Method and Apparatus for Depilation Using Pulsed Electromagnetic Radiation", filed Mar. 29, 1995, issued Nov. 4, 1997.

"Basic Principles: Microanatomy of the Skin; Derivatives of the Skin; Physiology of the Skin; Biochemistry of the Skin; Immunology of the Skin; Terminology of Skin Lesions; Examining the Skin; Basics of Medical Therapy".

"U.S. Health Care Industry Gears Up to 'Cure' Soviet Health Care Woes—Includes Text of Joint Statement on the Fourth Session of the Joint U.S.–USSR Commercial Commission Working Group on Medical Products and Supplies", Business America, Jul. 2, 1990, http://findarticles.com/p/articles/mi_m1052/is_n13_vIII/al_9154083, printed Apr. 5, 2007.

Adams, et al., "The Effect of Wavelength, Power and Treatment Pattern on the Outcome of Laser Treatment of Port–Wine Stains", British Journal of Dermatology, 117:487–494 (1987).

Alster, et al., "Comparison of Four Carbon Dioxide Resurfacing Lasers. A Clinical and Histopathologic Evaluation", Dermatol Surg., 25(3):153–158 (1999) Abstract Only.

Altshuler, et al., "Extended Theory of Selective Photothermolysis", Lasers in Surgery and Medicine, 29:416–432 (2001).

Altshuler, et al., "Optical Properties of Human Hair", Proc. SPIE, 2323:344–350 (1995).

Anderson, et al., "Lasers in Dermatology Provide a Model for Exploring New Applications in Surgical Oncology", International Advances in Surgical Oncology, 5:341–358 (1982).

Anderson, et al., "Selective Photothermolysis of Cutaneous Pigmentation by Q–Switched Nd:YAG Laser Pulses at 1064, 532, and 355 nm", Journal of Investigative Dermatology, 93(1):28–32 (1989).

Anderson, et al., "Selective Photothermolysis: Precise Microsurgery by Selective Absorption of Pulsed Radiation", Science, 220:524–527 (1983).

Anderson, et al., "The Optics of Human Skin", Journal of Investigative Dermatology, 77(1):13–19 (1981).

Astore, et al., "The Normal Trichogram of Pubic Hair", British Journal of Dermatology, 101:441–444 (1979).

Awan, "Argon Laser Treatment of Trichiasis", Ophthalmic Surgery, 17(10):658–660 (1986).

Basic Laser Physics and Visible Light Laser Surgery, pp. 1021–1022.

Berlien, et al., "Lasers in Pediatric Surgery", Progress in Pediatric Surgery, 25:5–22 (1990).

Bernstein, et al., "Scar Resurfacing with High–Energy, Short–Pulsed and Flashscanning Carbon Dioxide Lasers", Dermatol. Surg., 24(1):101–107 (1998) Abstract Only.

Boergen, et al., "Experimental Studies on Argon Laser Coagulation of Small Blood Vessels", Mod. Probl. Opthal., 20:174–183 (1979).

Buckley, et al., "Reflection Spectrophotometry. III. Absorption Characteristics and Color of Human Skin", Archives of Dermatology, 89:170–176 (1964).

Campbell, "Thermoablation Treatment for Trichiasis Using the Argon Laser", Australian and New Zealand Journal of Ophthalmology, 18(4):427–430 (1990).

Chernoff, et al., "SilkTouch: A New Technology for Skin Resurfacing in Aesthetic Surgery", J. Clin. Laser Med. Surg., 13(2):97–100 (1995) Abstract Only.

Dierickx, et al., "Thermal Relaxation of Port–Wine Stain Vessels Probed in Vivo: The Need for 1–10–Millisecond Laser Pulse Treatment", Journal of Investigative Dermatology, 105(5):709–714 (1995).

Dixon, et al., "Argon and Neodymium YAG Laser Therapy of Dark Nodular Port Wine Stains in Older Patients", Lasers in Surgery and Medicine, 6:5–11 (1986).

Dover, et al., Illustrated Cutaneous Laser Surgery: A Practitioners Guide, Appleton & Lange, Norwalk, CT, pp. 14–18 (1990).

Dreno, et al., "The Benefit of Chilling in Argon–Laser Treatment of Port–Wine Stains", Plastic and Reconstructive Surgery, 75(1):42–45 (1985).

Ebling, "Chapter 19: Biology of Hair Follicles", *Dermatology in General Medicine, Textbook and Atlas, Third Edition,* McGrew–Hill, pp. 213–219.

Ehlers, et al., "Cytophotometrische Untersuchungen zur Frage der Cancerogenen Wirkung von Rubinlaser–Licht", Der Hautarzt, 24:423–430 (1973) German Language.

Ehlers, et al., "Zur Frage der Kanzerogenen Wirkung von Rubinlaserstrahlen", Med. Klin, 68:1229–1238 (1973) English Abstract.

Finkelstein, et al., "Epilation of Hair–Bearing Urethral Grafts Using the Neodymium:YAG Surgical Laser", Journal of Urology, 146:840–842 (1991).

Finkelstein, et al., "Epilation of Hair–Bearing Urethral Grafts Utilizing the Neodymium:YAG Surgical Laser", Lasers in Surgery and Medicine, 10:189–193 (1990).

Gilchrest, et al., Chilling Port Wine Stains Improves the Response to Argon Laser Therapy, Plastic and Reconstructive Surgery, 69(2):278–283 (1982).

Goldman, "A Status on Laser Surgery", Contemporary Surgery, 3(2):18–24 (1973).

Goldman, "Chapter Eleven: Laser Techniques in Various Medical Specialties", *Laser Non–Surgical Medicine: New Challenges for an Old Application*, Technomic Publishing, Inc., pp. 213–238 (1991).

Goldman, "Comparison of the Biomedical Effects of the Exposure of Human Tissues to Low and High Energy Lasers", Annals New York Academy of Sciences, pp. 802–829 (1965).

Goldman, "Dermatologic Manifestations of Laser Radiation", Proceedings of the First Annual Conference on Biological Effects of Laser Radiation, Wachington, DC, Federation of American Societies for Experimental Biology, Suppl. 14:92–93 (1965).

Goldman, "Effects of New Laser Systems of the Skin", Arch Dermatol., 108:385–390 (1973).

Goldman, "Laser Action at the Cellular Level", JAMA, 198(6):173–176 (1966).

Goldman, "Laser Surgery for Skin Cancer", New York State Journal of Medicine, Oct., pp. 1897–1900 (1977).

Goldman, "The Skin", Arch Environ Health, 18:434–436 (1969).

Goldman, *Biomedical Aspects of the Laser*, Springer–Verlag, New York, Inc., pp. 9–21; 72–75; 96–97; 119–137; 168–182 (1967).

Goldman, et al., "Treatment of Basal Cell Epithelioma by Laser Radiation", JAMA, 189(10):171–173 (1964).

Goldman, et al., "Effect of the Laser Beam on the Skin—Preliminary Report", Journal of Investigative Dermatology, 40:121–122 (1963).

Goldman, et al., "Impact of the Laser on Nevi and Menalomas", Arahc Dermatol., 90:71–75 (1964).

Goldman, et al., "Investigative Studies with Quartz Rods for High Energy Laser Transmission", Medical Research Engineering, Fourth Quarter, pp. 12–17 (1967).

Goldman, et al., "Laser Surgery of Angiomas with Special Reference to Port–Wine Angiomas", XIII International Congress of Dermatology, Munich, Jul. 31–Aug. 5, 1967, vol. 2, Springer–Verlag, pp. 1388–1390 (1968).

Goldman, et al., "Laser Treatment of Tattoos: A Preliminary Study of Three Year's Clinical Experience", JAMA, 201(11):841–844 (1967).

Goldman, et al., "Long–Term Laser Exposure of a Senile Freckle", Arch Environ Health 22:401–403 (1871).

Goldman, et al., "Pathology of the Effect of the Laser Beam on the Skin", Nature, 197:912–914 (1963).

Goldman, et al., "Preliminary Investigation of Fat Embolization from Pulsed Ruby Laser Impacts of Bone", Nature, 221:361–363 (1969).

Goldman, et al., "Radiation from a Q–Switched Ruby Laser", JID, 44:69–71 (1965).

Goldman, et al., "Replica Microscopy and Scanning Electron Microscopy of Laser Impacts on the Skin", Journal of Investigative Dermatology, 52(1):18–24 (1969).

Goldman, et al., "The Biomedical Aspects of Lasers", JAMA, 188(3):230–234 (1964).

Goldman, et al., "The Effect of Repeated Exposures to Laser Beams", Acta. Derm. Venereol., 44:264–267 (1964).

Goldman, et al., Lasers in Medicine, (Goldman and Rockwell, eds.), Gordon and Breach, Science Publishers, Inc., pp. 259, 264, 265, 317, 366, 367 (1971).

Goldman, M, et al., "Treatment of Benign Pigmented Cutaneous Lesions", *Cutaneous Laser Surgery*, pp. 106–141 (1994).

Goldman, M., et al., "Laser Skin Resurfacing of the Face with a Combined CO2/Er:YAG Laser", Dermatol. Surg., 26(2):102–104 (2000) Abstract Only.

Gossman, et al., "Experimental Comparison of Laser Cryosurgical Cilia Destruction", Ophthalmic Surgery, 23(3):179–182 (1992).

Gossman, et al., "Prospective Evaluation of the Argon Laser in the Treatment of Trichiasis", Ophthalmic Surgery, 23(3):183–187 (1992).

Grossman, "Laser Targeted at Hair Follicies", American Society for Laser Medicine and Surgery Abstracts, No. 221 Abstract Only.

Grossman, et al., "Damage to Hair Follicles by Normal–Mode Ruby Laser Pulses", Journal of the American Academy of Dermatology, 35(6):889–894 (1996).

Haina, et al., "Possibilities for the Increase of the Coagulation Depth in Skin with the Argonlaser", Laser Optoelectronics in Medicine: Proceedings of the 7th Congress International Society for Laser Surgery and Medicine in Connection with Laser 87 Optoelectronics, (Waidelich, et al., eds.), pp. 539–542 (1988).

Hayashi, et al., "Q–Switched Ruby Laser Treatment of Ota's Nevus", J. Jpn. P.R.S., 13:705–714 (1993).

Hayes, et al., "Thermal Model for Retinal Damage Induced by Pulsed Lasers", Aerospace Medicine, 39(5):474–480 (1968).

Hedelund, et al., "CO2 Laser–Resurfacing: Increased Risk of Side Effects After UV–Exposure—An Experimental Animal Study", Lasers Surg. Med., 36(2):79–84 (2005).

Henderson, et al., "The 'light–touch': a Dermatology Handpiece Designed to Improve the Efficacy and Safety of Laser Treatment of Port–Wine Stains", Phys. Med. Biol., 32(12):1627–1630 (1987).

Ho, et al., "Laser Resurfacing in Pigmented Skin", Dermatol. Surg., 21(12):1035–1037 (1995) Abstract Only.

Huerter, et al., "Multiple Eruptive Vellus Hair Cysts Treated with Carbon Dioxide Laser Vaporization", Determol. Surg. Oncol., 13.3:260–263 (1987).

Jacques, "Laser–Tissue Interactions", Lasers in General Surgery, 72(3):531–558 (1992).

Khatri, et al., "Comparison of Erbium: YAG and Carbon Dioxide Lasers in Resurfacing of Facial Rhytides", Arch. Dermatol., 135(4):391–397 (1999) Abstract Only.

Kim, et al., "Regrowth of Grafted Human Scalp Hair after Removal of the Bulb", Dermatol. Surg., 21:312–313 (1995).

Kincade, "First Laser Hair–Removal System Gains FDA Clearance", Laser Focus World, 31(6):36, 38 (1995).

Kincade, "New Procedures Push Tissue Studies Beneath the Surface", Laser Focus World, Aug., pp. 57–63 (1995).

Kuhns, et al., "Laser Injury in Skin", Laboratory Investigation, 17(1):1–13 (1967).

Kuriloff, et al., "Pharyngoesophoageal Hair Growth: The Role of Laser Epilation", Case Reports, 98(4):342–345 (1988).

Lage, et al., "The Pathology of Laser Irradiation of the Skin and Body Wall of the Mouse", Laser Irradiation, 47(4):643–663 (1965).

Landthaler, et al., "Neodymium–YAG Laser for Vascular Lesions", Journal of the American Academy of Dermatology, 14(1):107–117 (1986).

Lask, et al., "Laser Skin Resurfacing with the SilkTouch Flashscanner for Facial Rhytides", Dermatol. Surg., 21(12):1021–1024 (1995) Abstract Only.

Lask, et al., "Neodymium:Yttrium–Aluminum–Garnet Laser for the Treatment of Cutaneous Lesions", Clinics in Dermatology, 13:81–86 (1995).

Maiman, "A Look at Things to Com: Biomedical Lasers Evolve Toward Clinical Applications", Hospital Management, Apr., pp. 39–41, (1966).

Matsumoto, et al., "Ruby Laser Treatment of Melanin Pigmented Skin Lesions using Toshiba Model LRT–301A Ruby Laser", Department of Plastic Surgery School of Medicine, Hokkaido University, 10(3):451–454 (1989) English Translation.

McKenzie, "Physics of Thermal Processes in Laser–Tissue Interaction", Phys. Med. Biol., 35(9):1175–1209 (1990).

Meloy, "The Laser's Bright Magic", National Geographic, Dec., pp. 858–881, (1966).

Mester, et al., "The Biomedical Effects of Laser Application", Lasers in Surgery and Medicine, 5:31–39 (1985).

Mester, et al., "The Effect of Laser Radiation on Hair Growth of the Mouse", Radiobiologia Radiotherapin, 9(5):621–626 (1968) English Translation.

Mester, et al., "Untersuchungen uber die hemmende bzw. fordemde Wirkung der Laserstrahlen", Langenbecks Arden fuer Chirurgie, 322:1022–1027 (1965) English Abstract.

Miyasaka, et al., "Basic and Clinical Studies of Laser for Hyperpigmented Skin Lesions", pp. 117–127 (1991).

Moy, et al., "Skin Resurfacing of Facial Rhytides and Scars with the 90–microsecond short pulse CO2 Laser. Comparison to the 900–microsecond dwell time CO2 Lasers and Clinical Experience", Dermatol. Surg., 24(12):1390–1396 (1998) Abstract Only.

Nakaoka, et al., "The Square and Uniform Intensity Ruby Laser for the Treatment of Pigmented Skin Lesions", Eur. J. Plast. Surg., 15:23–30 (1992).

Nelson, et al., "Dynamic' Cooling of the Epidermis During Laser Port Wine Stain Therapy", American Society for Laser Medicine and Surgery Abstracts, No. 253, Abstract Only.

Nelson, et al., "Dynamic Epidermal Cooling During Pulsed Laser Treatment of Port–Wine Stain", Arch Dermatol, 131:695–700 (1995).

Ohshiro, et al, "The Ruby and Argon Lasers in the Treatment of Naevi", Annals Academy of Medicine, 12(2):388–395 (1983).

Ohshiro, et al., Laser Treatment for Naevi, John Wiley & Sons, pp. 166–191, 195–201 (1995).

Ohtsuka, et al., "Ru Laser: Histological Studies and Clinical Experiences of Ruby Laser Treatment", 11(4):107–115 (1991) English Abstract.

Oliver, "Dermal–Epidermal Interactions and Hair Growth", Journal of Investigative Dermatology, 96:76s (1991).

Ono, et al., "Histopathological Alteration of Skin after Irradiation of Ruby Laser", 11(4):99–105 (1991).

Oshry, et al., "Argon Green Laser Photoepilation in the Treatment of Trachomatous Trichiasis", Ophthalmic Plastic and Reconstructive Surgery, 10(4):253–255 (1994).

Parrish, et al., "Selective Thermal Effects with Pulsed Irradiation from Lasers: From Organ to Organelle", The Journal of Investigative Dermatology, 80(6):75s–80s (1983).

Paul, et al., "The Effect of Temperature and Other Factors on Selective Microvascular Damage Caused by Pulsed Dye Laser", Journal of Investigative Dermatology, 81(4):333–336 (1983).

Philipp, et al., "Ten Years of Laser Treatment of Congenitial Vascular Disorders", SPIE, 2327:44–53 (1994).

Polla, et al., "Melanosomes Are a Primary Target of Q–Switched Ruby Laser Irradiation in Guinea Pig Skin", Journal of Investigative Dermatology, 89(3):281–286 (1987).

Random House Webster's College Dictionary, pp. 286, 425, 1044 (1999).

Riggle, et al, "Chapter 3: Laser Effects on Normal and Tumor Tissue", *Laser Applications in Medicine and Biology*, pp. 38–65 (1970).

Rosenfeld, et al., "The Treatment of Cutaneous Vascular Lesions with the Nd:YAG Laser", Annals of Plastic Surgery, 21(3):223–230 (1988).

Rosenfeld, et al., "Treatment of Cutaneous and Deep Vascular Lesions with the Nd:YAG Laser", Lasers in Surgery and Medicine, 6:20–23 (1986).

Ross, et al., "Long–Term Results after CO2 Laser Skin Resurfacing: A Comparison of Scanned and Pulsed Systems", J. Am. Acad. Dermatol., 37(5 Pt 1):709–718 (1997).

Schrimer, "Simultaneous Thermal and Optical Breakdown Mode Dual Laser Action", Ophthalmologica, 205:169–177 (1992).

Shapshay, et al., "Neodymium–YAG Laser Photocoagulation of Hemangiomas of the Head and Neck", Laryngoscope, 97:323–330 (1987).

Sheblakov, et al., "New Applications for YAG:ND Laser in Medicine", Proceedings of the 2nd School of Young Scientists of the General Physics Institute of Russia, Moscow, p. 20 (1989) English Translation.

Sheblakov, et al., "Novel Use of Nd:YAG Laser in Medicine", Methods of Modern Optics in General Physics Problems Solution, Scientific Proceedings, p. 20 (1989) English Translation.

Sherwood, et al., "Effect of Wavelength of Cutaneous Pigment Using Pulsed Irradiation", Journal of Investigative Dermatology, 92(5):717–720 (1989).

Shimbashi, et al., "Ruby Laser Treatment of Pigmented Skin Lesions", Aesth. Plast. Surg., 19:225–229 (1995).

Shimizu, et al., "Ruby Laser and Its Medical Applications", 45(4):353–355 (1990).

Solomon, et al., "Histopathology of the Laser Treatment of Port–Wine Lesions", Journal of Investigative Dermatology, 50(2):141–146 (1968).

Stedman's Medical Dictionary, Twenty–Third Edition, p. 203 (1976).

Supraherent Industries, Ltd., "LadyLaze" Information downloaded from http://web.archive.org/web/19961109160641/www.linkcafe.co.uk/business/supraherent/set.html.

Tan, et al., "Laser Therapy for Selected Cutaneous Vascular Lesions in the Pediatric Population: A Review", Pediatrics, 82(4):652–662 (1988).

Tan, et al., "Treatment of Children with Port–Wine Stains Using the Flashlamp–Pulsed Tunable Dye Laser", NEJM, 320(7):416–421 (1989).

Tanino, et al., "Development of Ruby Laser System for Medical Use", Journal of the Japanese Society for Laser Surgery and Medicine, 11(4):93–99 (1991) English Translation.

Taylor, et al., "Treatment of Tattoos by Q–Switched Ruby Laser", Arch Dermatol, 126:893–899 (1990).

The American Heritage Dictionary, Office Edition, Third Edition, pp. 191, 249 (1994).

The American Heritage Dictionary, Second College Edition, pp. 121, 315 (1985).

Trelles, et al., "A Clinical and Histological Comparison of Flashscanning Versus Pulsed Technology in Carbon Dioxide Laser Facial Skin Resurfacing", Dermatol. Surg., 24(1):43–49 (1998) Abstract Only.

Trelles, et al., "Penetration Depth of Ultrapulse Carbon Dioxide Laser in Human Skin", Dermatol. Surg., 22:863–865 (1996).

Van Gemert, et al., "A Model Approach to Laser Coagulation of Dermal Vascular Lesions", Arch Dermatol Res, 270:429–439 (1981).

Van Gemert, et al., "Is There An Optimal Laser Treatment for Port Wine Stains", Lasers in Surgery and Medicine, 6:76–83 (1986).

Van Gemert, et al., "Time Constants in Thermal Laser Medicine", Lasers in Surgery and Medicine, 9:405–421 (1989).

Van Gemert, et al., "Treatment of Port–Wine Stains: Analysis", Medical Instrumentation, 21(4):213–217 (1987).

Watanabe, et al., "Comparative Studies of Femtosecond to Microsecond Laser Pulses on Selective Pigmented Cell Injury in Skin", Photochemistry and Photobiology, pp. 757–762 (1991).

Watanabe, et al., "The Effect of Pulse Duration on Selective Pigmented Cell Injury by Dye Lasers", Abstracts, 88(4):523 (1987) Abstract Only.

Welch, et al., "Evaluation of Cooling Techniques for the Protection of the Epidermis During ND–YAG Laser Irridiation of the Skin", Neodymium—YAG Laser in Medicine and Surgery (Joffe, et al., eds.), Elsevier Science Publishing, Inc., pp. 196–204 (1983).

Werner, et al., Treatment of Haemungiemas with Neodymium:YAG Laser (Nd:YAG Laser), Laryngo–Rhino–Otol, 71:388–395 (1992) English Translation.

Wheeland, "Clinical Uses of Lasers in Dermatology", Lasers in Surgery and Medicine, 16:2–23 (1995).

Wheeland, "Microanatomy and Physiology of the Skin".

Yules, et al., "The Effect of Q–Switched Ruby Laser Radiation on Dermal Tattoo Pigment in Man", Arch Surg, 95:179–180 (1967).

Saitoh, et al. "Human Hair Cycle", Journal of Investigative Dermatology, 54(1):65–81 (1970).

Leon Goldman, M.D., "Biomedical Aspects of the Laser", Springer–Verlag, New York, Inc. (1967), pp. 24.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–3, 6–8, 11, 17–20, 27, 28, 30 and 32 is confirmed.

Claims 12–14 are cancelled.

New claims 33–59 are added and determined to be patentable.

Claims 4, 5, 9, 10, 15, 16, 21–26, 29 and 31 were not reexamined.

33. A method as claimed in claim 32, wherein the element is a converging element.

34. A method as claimed in claim 33, where in the tissue surrounding the hair follicles is not significantly damaged.

35. A method as claimed in claim 33, wherein pressure is applied to the skin surface during the applying step.

36. A method as claimed in claim 35, wherein such pressure is positive pressure.

37. A method as claimed in claim 35, wherein such pressure is negative pressure.

38. A method as claimed in claim 32, 33, 43, 45, 34, 44, 48, 49, 51, 53, 56, 57, or 35, wherein the optical radiation is produced by a laser.

39. A method as claimed in claim 38, wherein the laser is a Nd:YAG laser.

40. A method as claimed in claim 38, wherein the laser is an alexandrite laser.

41. A method as claimed in claim 32, 33, 43, 45, 34, 44, 48, 49, 51, 53, 56, 57, or 35, wherein the optical radiation is produced by a light source producing a wavelength or wavelengths between 680 and 1200 nanometers.

42. A method as claimed in claim 32, 33, 43, 45, 34, 44, 48, 49, 51, 53, 56, 57, or 35, wherein the method of removal causes significant permanent hair loss.

43. A method as claimed in claim 32, wherein the element is a non-converging element.

44. A method as claimed in claim 43, where in the tissue surrounding the hair follicles is not significantly damaged.

45. A method as claimed in claim 32, where in the tissue surrounding the hair follicles is not significantly damaged.

46. A method as claimed in claim 45, wherein the wavelength is between 700–1200 nanometers.

47. Method as claimed in claim 46, wherein the fluence is between 10 and 100 J/cm$^2$.

48. A method as claimed in claim 47, wherein a portion of the skin region is cooled before the applying step.

49. A method as claimed in claim 48, wherein a portion of the skin region is cooled during the applying step.

50. A method as claimed in claim 33, 43, 45, 34, 44, 47, 48, or 49, wherein the element is contained within an applicator that is in contact with the skin surface during the applying step.

51. A method as claimed in claim 32, wherein the element is contained within an applicator that is in contact with the skin surface during the applying step.

52. A method as claimed in claim 33, 43, 45, 34, 44, 47, 48, 49, or 51, wherein the optical radiation is applied from air to the skin region.

53. A method as claimed in claim 32, wherein the optical radiation is applied from air to the skin region.

54. A method as claimed in claim 33, 43, 45, 34, 44, 48, 49, 51, or 53, wherein the element includes a transparent surface.

55. A method as claimed in claim 54, wherein the surface is sapphire.

56. A method as claimed in claim 32, wherein the element includes a transparent surface.

57. A method as claimed in claim 56, wherein the surface is sapphire.

58. A method as claimed in claim 43, 45, 34, 44, 48, 49, 51, 53, 56, or 57, wherein pressure is applied to the skin surface during the applying step.

59. A method as claimed in claim 43, 45, 34, 44, 48, 49, 51, 53, 56, or 57, wherein such pressure is negative pressure.

* * * * *